United States Patent [19]

Brunnett et al.

[11] 4,008,400
[45] Feb. 15, 1977

[54] TRANSVERSE TOMOGRAPHY SYSTEM HAVING MULTIBEAM ORBITAL SCANNING WITH ALL BEAMS OFFSET FROM THE CENTER OF ORBIT

[75] Inventors: Carl J. Brunnett, Mayfield Heights, Ohio; Jerome R. Cox, Jr., St. Louis; Donald L. Snyder, Clayton, both of Mo.; Rodney A. Mattson, Mentor, Ohio

[73] Assignee: Picker Corporation, Cleveland, Ohio

[22] Filed: Nov. 28, 1975

[21] Appl. No.: 635,952

Related U.S. Application Data

[63] Continuation-in-part of Ser. No. 559,411, March 18, 1975, Pat. No. 3,976,885.

[52] U.S. Cl. .............................. 250/445 T; 250/490
[51] Int. Cl.² ........................................ G01M 23/00
[58] Field of Search ............ 250/445 T, 490, 363 S, 250/402, 416, 360

[56] References Cited

UNITED STATES PATENTS

| | | | |
|---|---|---|---|
| 3,106,640 | 10/1963 | Oldendorf | 250/360 |
| 3,612,865 | 10/1971 | Walker | 250/445 T |
| 3,684,886 | 8/1972 | Muehllegner | 250/445 T |
| 3,752,982 | 8/1973 | Jaszczak | 250/445 T |
| 3,778,614 | 12/1973 | Houmsfield | 250/445 T |
| 3,946,234 | 3/1976 | Houmsfield | 250/445 T |

Primary Examiner—Alfred E. Smith
Assistant Examiner—B. C. Anderson
Attorney, Agent, or Firm—Watts, Hoffmann, Fisher & Heinke

[57] ABSTRACT

A dual axial scanner in a transverse tomography system collects nonredundant data throughout one or more substantially 360° orbital scan paths with uniform motion about a patient. A set of N X-ray beams scans the patient in a manner to allow collection of two sets of non-redundant data corresponding to a pair of 180° scans in each 360° scan. Overall time to conduct the study is decreased, and the number of required accelerations and decelerations of the assemblies is minimized.

Adjacent beams of radiation are separated by an angle $\alpha$, which is one degree in the preferred embodiment to provide a radiation field of $$\left(\frac{N-1}{2}\right)\alpha$$

degrees on either side of a center of the radiation field. The source and detector assemblies are positioned prior to the first orbit such that the field center is offset a distance D from a center of orbit lying in the orbital plane. The source and detector assemblies are mounted for rotation through a rotation angle $\phi_j$ about an orbital source axis which passes through the source assembly at a distance d from the center of orbit. While maintaining the offset distance D, the assemblies orbit the patient, and radiation intensity data is collected at predetermined angles $\gamma_j$ of orbit.

In one embodiment for doubling the effective field size of the patient scanned, the source and detector assemblies are rotated about the source axis to provide the distance D. From an initial position on the center of orbit, the assemblies are rotated by an offset angle $$\phi_o = \left(\frac{N-1}{2}\right)\alpha + \frac{\alpha}{2R}$$

degrees where R is the number of total orbits selected to constitute a complete study. In another embodiment for single field exposure the source and detector assemblies are rotated by the offset angle $\phi$ defined substantially by the equation $$\phi_o = b\frac{\alpha}{2} - \frac{\alpha}{4R}$$

degrees, where "b" is zero for an odd number N of detectors and is one for an even number N of detectors. For multiorbit studies, the assemblies are rotated between orbits by an amount $$\Delta\phi = \frac{\pm\alpha}{R} \text{ or } \frac{-\alpha}{2R}$$

degrees depending on the study.

41 Claims, 29 Drawing Figures

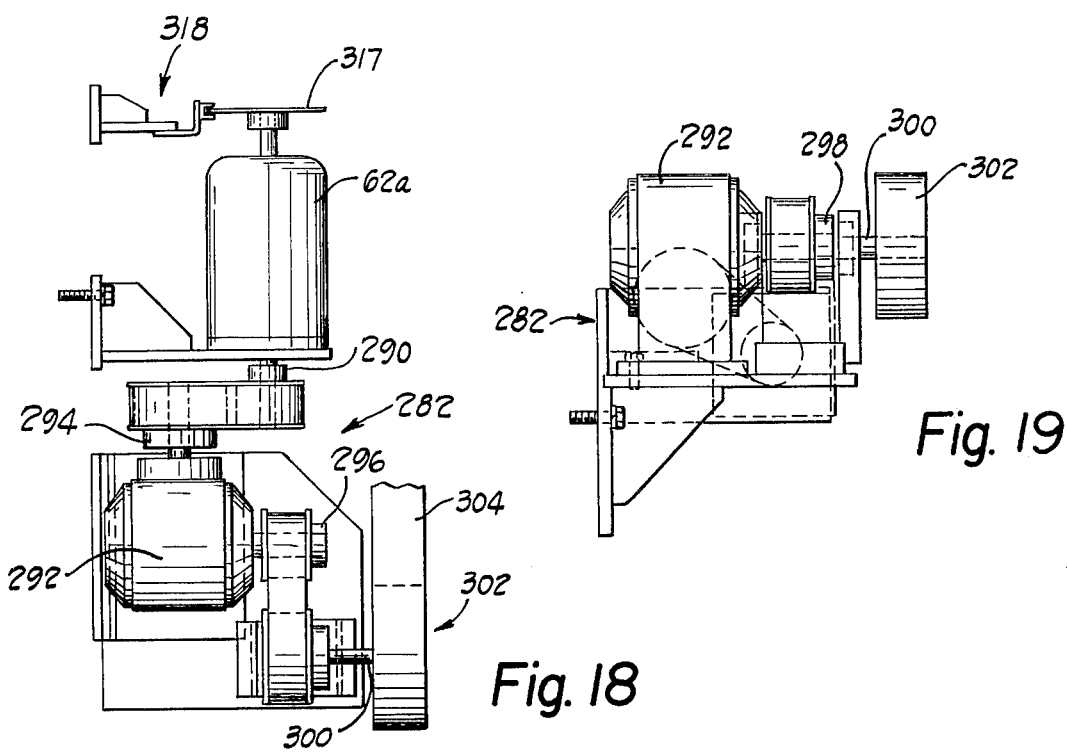
Fig. 18
Fig. 19
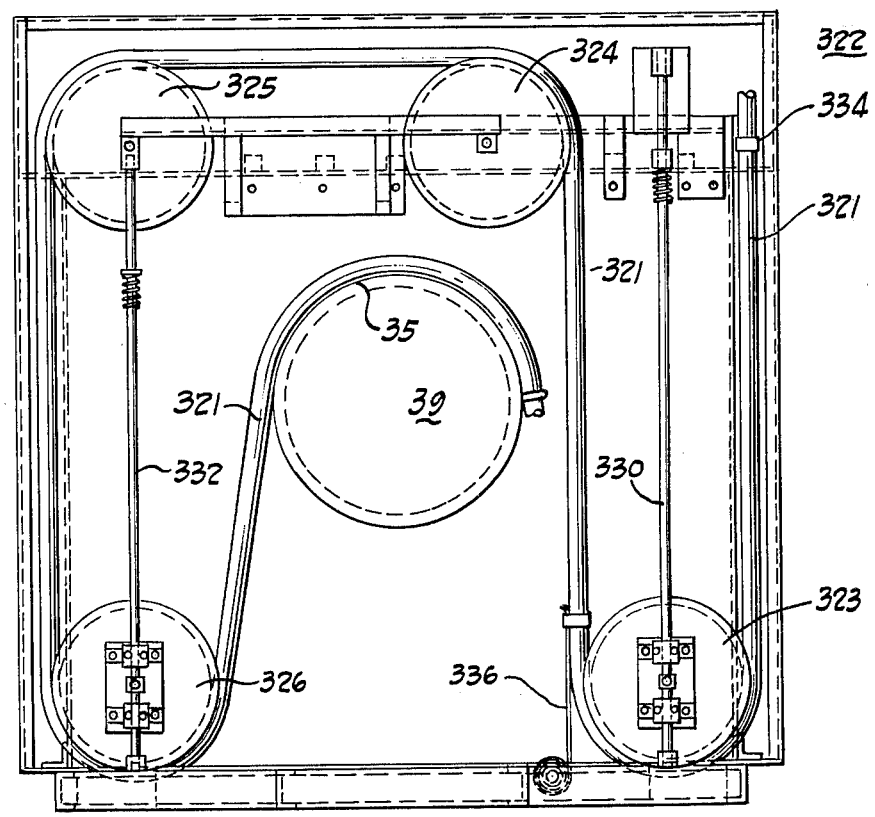
Fig. 20

TRANSVERSE TOMOGRAPHY SYSTEM HAVING MULTIBEAM ORBITAL SCANNING WITH ALL BEAMS OFFSET FROM THE CENTER OF ORBIT

REFERENCES TO RELATED AND RELEVANT PATENTS AND APPLICATIONS

This application is a continuation-in-part of application entitled TOMOGRAPHY SYSTEM HAVING NONCONCURRENT COMPOUND AXIAL SCANNING, Ser. No. 559,411, filed Mar. 18, 1975 U.S. Pat. No. 3,976,885.

U.S. Pat. No. 3,621,247, issued Nov. 16, 1971, entitled "X-Ray Tire Inspection Apparatus", (here the TIRE patent).

U.S. Pat. No. 3,803,415, issued Apr. 9, 1974, entitled METHOD AND APPARATUS FOR INSPECTING TIRES WITH X-RAY (here the X-RAY patent);

United States Patent Application Ser. No. 301,529 filed on Oct. 27, 1972, entitled METHOD AND APPARATUS FOR INSPECTING TIRES (here the METHOD patent application);

United States Patent Application Ser. No. 95,859, filed Dec. 7, 1970, entitled TIRE INSPECTION APPARATUS (here the APPARATUS patent application).

BACKGROUND OF THE INVENTION

This invention relates generally to the nondestructive examination of objects by penetrative radiation and, more particularly, relates to clinical methods and apparatus for tomographically examining an internal section of a patient by scanning a set of beams of X-radiation from an orbiting radiation source in a plane transverse to the patient.

FIELD OF THE INVENTION

A conventional radiograph is a two-dimensional shadow image of a three-dimensional subject. The depth dimension is not apparent as all interior portions of the subject appear to be in a single plane. As a consequence, a conventional radiograph fails to provide necessary detail as to spacial location of a condition, is difficult to interpret, and may not reveal a condition which exists.

Tomographic procedures have been developed to fulfill some objectives which are unobtainable by conventional radiographical procedures. In tomography, an image of a cross-sectional plane of a specimen is developed by sequentially directing X-rays through the subject from a plurality of directions. Early tomographic systems utilized a radiation sensitive recording plate whose movement was coordinated with movement of a radiation source. The source-recording plate pair moved about a system axis passing through the subject and recorded a cross-sectional image of the subject in a plane which is transverse to the axis of the X-ray beam. The movement of the source-recording plate pair was such that elements in the selected cross-sectional plane of the subject were continuously scanned by the beam. This scanning technique resulted in substantially continuous change in the spatial relationship among the film source and the elements of the subject. This change blurred images of the elements out of the plane with the result that an image in a lateral plane of the specimen was produced.

Other tomographic procedures have been proposed which develop an image of the subject in a plane which includes the axis of the X-ray beam. Tomography which produces an image in a plane which includes the X-ray beam axis is known as transverse section tomography.

Prior Art

With one of these transverse section proposals, a radiation sensitive detector orbited in aligned synchronism with the radiation source. More specifically, the source/detector pair was angularly rotated in a plane as the beam of radiation passed through the patient. The patient and source were periodically translated relatively in the plane of rotation, and the rotation was then repeated. The angular rotation was about a system axis which passed through the patient, and the beam of radiation passed through the system axis. By passing the beam through the system axis as the source was rotated, a small central region within the specimen could be isolated by cancelling the effects of all areas remote from the central region. Translation of the specimen allowed an image of a section of the specimen in the plane of rotation to be reconstructed as a video image displaying an integration of information from a series of small central areas.

Another proposal for transverse section tomography suggested the use of a plurality of radiation detectors disposed in a line in the direction of translation in an attempt to increase the speed of the scan. Even with the multiple detectors, these proposals using an orbital scan motion coupled with a linear translation motion resulted in a system requiring long scanning times to provide images of limited size and quality.

A scanning system is described in Kuhl, et al., "Transmission Scanning, A Useful Adjunct to conventional Emission Scanning for Accurately Keying Isotope Deposition to Radiographic Anatomy," Radiology, 1966, Vol. 87, pp. 278–284. The referenced "Emission" scanning system uses a detector for scanning a patient who had previously been administered radioisotope. The detector measures intensity values of the radiation as it is emitted from the patient. Transmission scanning differs from emission scanning in that transmission scanning uses a radiation source to transmit a beam of radiation through the patient instead of radiation emitted by an administered radioisotope. An emission scanning tomographic system is described in D. E. Kuhl and R. Q. Edwards, "Cylindrical and Section Radioisotope Scanning of the Liver and Brain," Radiology, Vol. 83, No. 5, pp. 926–936; 1964.

The science of reconstruction tomography using transverse section scanning has evolved to a translational scanning system where a radiation source/detector pair scans a patient with a beam of radiation emitted as the source detector/pair are translated in a plane containing the section of the patient to be examined. The angular orientation of the beam is changed from one scan to another. The detected intensity of the beam is recorded for computing X-ray transmission or X-ray absorption characteristics through the scanned section. A plot of these characteristics provides a reliable image of the internal structure of the patient in the scanned plane. Transverse section scanning is also described in the Kuhl, et al., references.

Reconstruction tomography commonly utilizes a back projection computational process technique for processing the radiation intensity data to reconstruct the image. The detected value of the X-ray transmission intensity through the patient is projected back along the path of the beam that produced the measured value of radiation. The values of radiation transmission intensity measured during each scan are back projected for a scan-by-scan build-up of the image. More specifically, each value of the radiation transmission as it is projected back is kept constant, and the respective values of each back projection at points of intersection are added together. This technique is described in Kuhl, "A clinical Radioisotope Scanner for Cylindrical and Section Scanning," PROC. SYMP., Athens 1964, Medical Radioisotope Scanning, I.A.E.A., Vienna, 1, 273, 1964.

The back projection technique has been improved with the introduction of filtered back projections and data processing using Fourier analysis. A formula for realizing Fourier reconstruction using filtered back projections is set forth in Chesler, THREE-DIMENSIONAL RECONSTRUCTION TECHNIQUE, J. NUCL. MED., 1974.

In the above-described translational scanning system for transverse section scanning, a linearly disposed array of X-ray source/detector pairs were to rectilinearly scan a specimen along a path at a first angle with respect to an axis passing through the specimen. Radiation intensity values were to be recorded during the rectilinear scan. After completing a rectilinear scan of the specimen at the first angle the source/detector pair were to be angularly indexed. A second rectilinear scan was to be performed on the specimen along a second path at a second angle with respect to the axis, and so forth.

After rectilinearly scanning along paths covering 180° of angles with respect to the axis, the intensity data collected from radiation measurements were processed utilizing a method of successive approximations. A reconstructed image was generated representing the X-ray transmission of X-ray absorption coefficients lying in a section of the specimen.

Apparatus for performing the rectilinear scans was massive and required large motive forces for linearly accelerating, decelerating and reversing direction of the array of the source-detector pair. Contrary to an optimum scanning motion which would minimize the number of accelerations and decelerations, a 180 translational and 179 rotational accelerations and decelerations, as well as 179 direction changes during translation were required to complete a study. In addition, the large number of accelerations, decelerations and direction changes resulted in a system requiring an undue amount of scanning time. A minimum scanning time is essential to minimize the time required for completing a study in order to minimize the effects of changing conditions in the patient, to increase patient throughput, to minimize discomfort and to utilize the equipment most efficiently.

A prior proposal has suggested the transverse section scanning of a specimen by a source/detector pair which orbited about a system axis which itself orbited about a system center passing through the specimen. The system axis traced a circle of small diameter about the system center as the source-detector pair orbited about the system axis. Apparatus for revolving the source/detector pair in such a proposal is subjected to extreme inertial forces due to the mass of the source/detector pair. Practicality has shown that the system axis should be stationary at the system center if exact image reconstruction is to be achieved with the simplest system. Furthermore, the proposal failed to disclose the relationships among the rotation about the system axis, the optimum angles of radiation measurement, the speed of orbit about the system axis, and the speed of rotation of the system axis in the circular motion.

The prior art has also suggested a transverse section, transmission scanning system which would orbit a source-detector pair about a stationary system axis through the specimen. Concurrently with the orbiting, the source-detector pair were to be rotated in the plane of the orbit about an orbiting source axis which passed through the source. The use of an array of detectors disposed in the plane of orbit was also suggested. The proposal failed to disclose the relationships amont the rotational and orbital movements of the source and detectors and the orientations of the source and detectors at which measurements were to be taken if exact reconstruction was to be achieved. The proposal also failed to disclose apparatus for implementing the suggested system. Furthermore, the proposal did not recognize that data collected by this dual rotational motion may not be in the sequence required by the particular reconstruction algorithm used in processing the collected data. Without this recognition and a solution of the recognized problem, data collected by this scanning motion would not provide clinically acceptable results in an acceptable period of time.

Furthermore, these previously suggested tomographic systems were generally constructed to provide a limited field size from which an image could be reconstructed. Many applications require a large field size; for example, whole body studies.

SUMMARY OF THE INVENTION

The noted and other deficiencies of the art are overcome by providing a transverse section, reconstruction tomographic system which orbitally scans a patient with a set of N beams of radiation in a manner which allows the collection of nondulplicate data through greater than 180° orbital scans. A one revolution orbital scan allows the collection of data otherwise requiring a pair of substantially one half revolution orbits. This minimizes not only the number of overall accelerations, decelerations, and orbital direction reversals, but also the overall time required to complete a study. The disclosed tomographic system also provides a method of scanning which increases the size of the field of scan from which an image is reconstructed. An increase of up to 100 percent is achieved over the field size produced by methods not employing this aspect of the invention, making the invention particularly useful in whole body studies.

The transverse section tomographic system has a radiation source assembly which emits a set of N X-ray beams each having an axis in an orbital plane. The source assembly is orbital in an arc about a system axis which is normal to the orbital plane and intersects it at a center of orbit. The source assembly is rotatable about a source axis which is spaced from and parallels the source axis. The beams of the set are directed radially of the source axis with the beams of each adjacent pair separated by a separation angle $\alpha$.

Accordingly, the set of beams defines a radiation field spanning $(N-1/2)\ \alpha$ degrees on each side of a field centerline in the plane of orbit and passing through a patient. The source assembly is initially positioned such that the field centerline is offset from the system axis by an offset distance D. The assembly is then orbited about the system axis while maintaining the offset distance.

A detector assembly is provided. The detector assembly has a plurality of radiation detectors each aligned with a different one of the beams of radiation. The detector assembly measures the intensity of each of the beams to determine the X-ray absorption or transmission coefficients within the interior section of the patient. An image is then reconstructed from the X-ray transmission or absorption coefficients at coplanar reconstruction points $m(t_k, \theta_n)$ about an origin in the orbital plane. For simplicity of description, the origin is selected coincident with the center or orbit.

The tomographic system comprises a support apparatus having a pair of arms. The support apparatus is rotatable about a centrally located pivot which has an axis coincident with the source axis. The source and detector assemblies are mounted for rotation through a rotation angle $\phi$ about the source axis. The source axis extends through one of the arms of the support apparatus. Rotation of the support apparatus about the system axis causes the source and detector assemblies to orbit through an orbit angle $\gamma$. As the support apparatus rotates about the system axis, the beams from the source assembly trace a scanning path which encompasses the array of the measurement points.

In the preferred embodiment two sets of data totaling 180 views and corresponding to a pair of approximately 179° orbits are provided from a single 359° orbital scan. The source and detector assemblies are positioned prior to rotation of the support apparatus such that the radiation field centerline is displaced the offset distance D from the center of orbit. The positioning of the assemblies (assuming the assemblies to initially be positioned so that the field centerline intersects the system axis) is by rotation of the source and detector assemblies about the source axis through an offset angle $\Phi_o$. The offset angle $\Phi_o$ is controlled to maintain the offset distance D, as the support apparatus rotates through the substantially 359° orbit about the system axis. Because passage of the X-ray beam through the human body in the first one-half of an orbit is substantially bidirectionally related to beam passage during the second one-half of the 359° orbit, the two half orbits provide two complete sets of nonduplicate data of approximately 179° each.

To produce reconstructed images of high resolution, several substantially full revolution orbits may be performed. In one scanning embodiment to provide a single field image, the source and detector assemblies are rotated through the offset angle characterized substantially by the equation $$\Phi_o = \frac{\alpha}{2} - \frac{\alpha}{4R} \text{ degrees.}$$

if N is even, or $$\Phi_o = -\frac{\alpha}{4R}$$

if N is odd, where R is the total number of orbits required to complete a study. The radius of orbit $d$, is the distance between the orbital and source axes. The radius $d$ has a preselected value for any given study. The single field offset distance $D_1$ is characterized substantially as $$D_1 = d \sin - \left(\frac{\alpha}{2} - \frac{\alpha}{4R}\right)$$

if N is even or $D_1 = d \sin$ $$d \sin - \left(\frac{\alpha}{4R}\right)$$

if N is odd. After completion of each orbit, the source axis by an incremental angle $\Delta \Phi$ characterized substantially as $$\Delta\Phi = -\frac{\alpha}{R} \text{ or } -\frac{\alpha}{2R} \text{ degrees.}$$

In the case where $$\Delta\Phi = -\frac{\alpha}{R},$$

R is limited to an integer number of substantially full revolution orbital scans. This choice provides the best data mix as a given detector in the detector assembly measures alternate data points used in reconstructing the set of reconstruction points m $(t_k, \theta_n)$. This provides an interlacing which averages out any error inherent in a single detector.

In the case where $$\Delta\Phi = \frac{-\alpha}{2R},$$

2R is limited to the integer number of substantially full revolution scans required to complete the study. For this choice a given detector measures successive data points used in reconstructing the reconstruction points $m(t_k, \theta_n)$.

In another scanning embodiment the radiation field centerline is offset from the system axis by a double field distance $D_2$ having a value which effectively allows doubling of the size of the scan field from which the image is reconstructed. The offset distance $D_2$ is characterized substantially as $$D_2 = d \sin \left[\left(\frac{N-1}{2}\right)\alpha + \frac{\alpha}{2R}\right]$$

and the offset angle $\Phi_o$ is characterized as $$\Phi_o = \left(\frac{N-1}{2}\right)\alpha + \frac{\alpha}{2R}$$

(where it again it is assumed the source and detector assemblies are initially positioned with the field centerline intersecting the system axis). The direction of the offset angle $\Phi_o$ may be in either rotary direction about the source axis. For this doubled field size scan, R is defined as the total number of substantially full revolution orbital scans required to complete a study. For multi-orbital scans, after completion of each orbit the source and detector assembly is indexed about the source axis by an increment angle $\Delta\Phi$ characterized substantially as $$\Delta\Phi = \frac{\alpha}{2R}$$

degrees.

During each orbit in the above-described scanning embodiments intensity measurements are taken at points in the orbit when the assemblies define the angle $\phi_j$, of rotation and the angle $\gamma_j$ of orbit to be substantially:

$$\phi_j = \sin^{-1}(k\Delta t/d) + \phi_R \text{ and } \gamma_j = \phi_j + n\ \Delta\theta,$$

where $d$ represents the distance between the system and source axes, $\Phi_R$ is characterized as $$\Phi_R = \Phi_o + (r-1)\ \Delta\ \Phi$$

with the letter "$r$" defining the number $r^{th}$ orbit in the sequence of R total orbits, and $k$ and $n$ are integers including zero.

It is accordingly an object of the present invention to provide an improved method and apparatus for tomographically scanning a patient with an orbiting pair of radiation source and detector assemblies.

BRIEF DESCRIPTION OF THE DRAWINGS

FIGS. 18–19 are illustrations of a delta frame drive arrangment used in the apparatus of FIGS. 14–17; and FIG. 20 is an illustration of a cable take-up mechanism used in the apparatus of FIGS. 14–17.

DETAILED DESCRIPTION OF A PREFERRED EMBODIMENT

Figure 1:
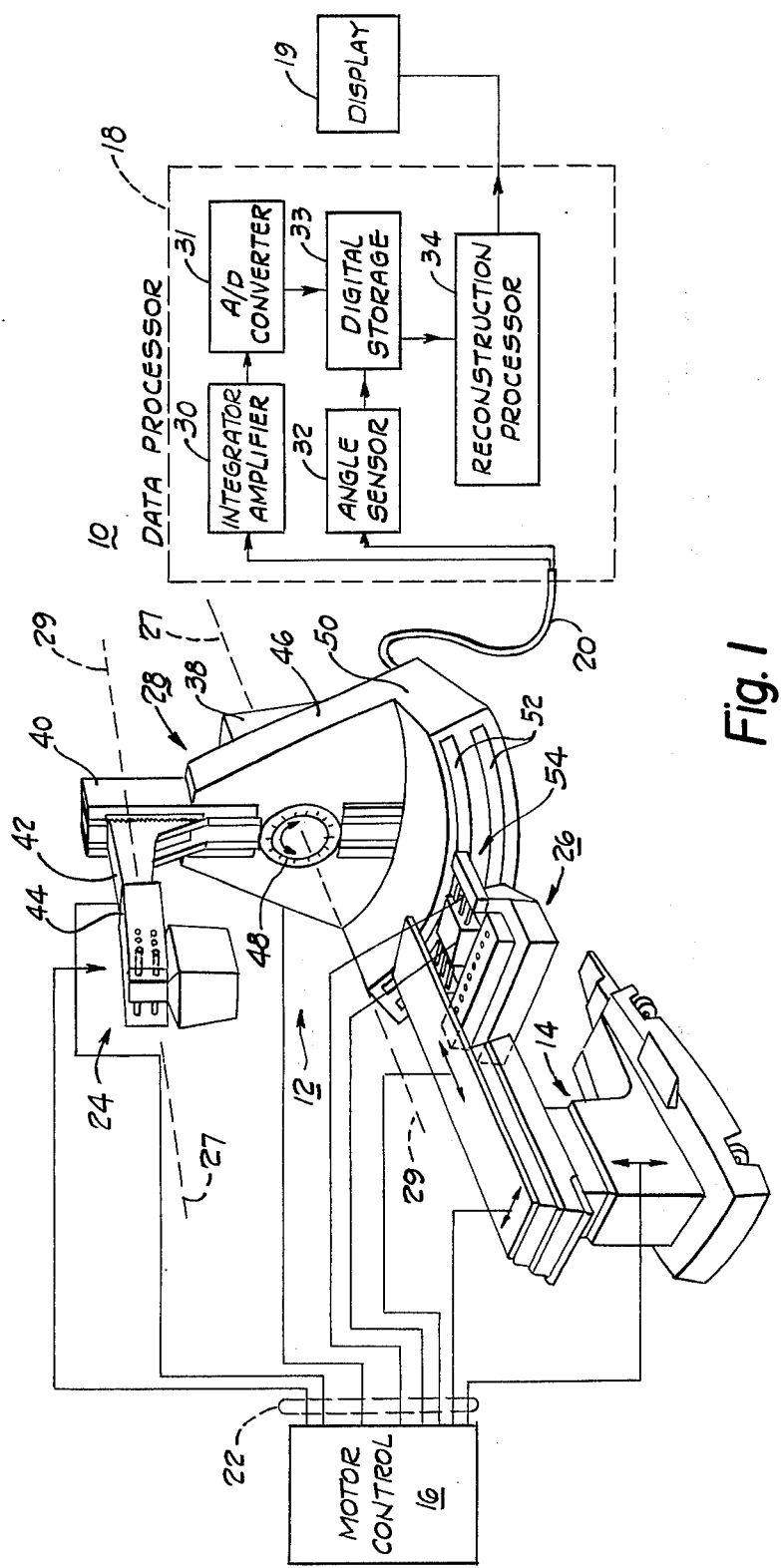
FIG. 1 is a combined perspective and functional representation of a reconstruction tomographic system having scanning apparatus according to this invention.

Referring to FIGS. 1–5 a transverse section, reconstruction tomographic system is shown generally at 10. The tomographic system 10 includes scanning apparatus 12, a patient supporting stretcher 14, a motor controller 16, a data processor 18 and a display 19. The scanning apparatus 12 is operable in response to the controller 16 for X-ray scanning a transverse section of a patient on the stretcher 14 through a multiplicity of coplanar angles. The scanning apparatus 12 derives radiation intensity data from collimated beams of X-rays after they pass through the patient. The collected data is coupled by a data cable line 20 to the data processor 18. The data processor 18 reconstructs an image of the transverse section of the patient by computing the coefficients of X-ray absorption or transmission. The reconstructed image is provided by a plot of the coefficients on the display 19.

The stretcher 14 movably supports the patient in position for examination near the scanning apparatus 12. The stretcher 14 is mounted on wheels and is motor driven in response to signals on a set of lines 22 from the controller 16 for elevating and translating the patient into position.

The scanning apparatus 12 comprises a radiation source assembly 24, a radiation detector assembly 26, and support structure 28 which supports the source and detector assemblies 24, 26 diametrically of the patient. The radiation source assembly 24 provides a plurality of collimated, coplanar beams of X-radiation to the radiation detector assembly 26. The radiation detector assembly 26 has a plurality of radiation detectors each aligned for receiving an associated one of the beams. Each radiation detector generates output signals indicative of the intensity of the associated X-ray beam.

The support structure 28 is rotated about a system axis 27 through a sequence of approximately one half revolutions or continuously through full revolutions. The structure is rotated at speeds up to 30 rpm by a stepping motor 60 under control of the motor controller 16. Rotation of the support structure 28 provides relative motion between a patient on the stretcher 14 and the radiation beams. The support structure 28 maintains the radiation detector assembly 26 in alignment with the radiation source assembly 24 for reception of the radiation beams.

Figure 11:
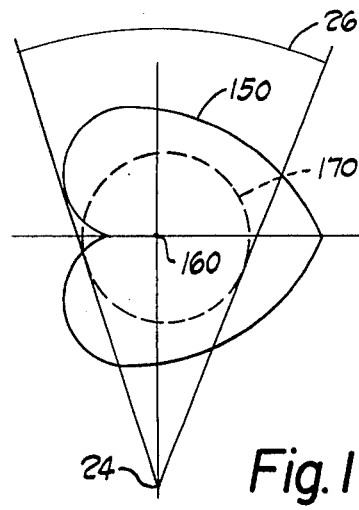
FIG. 11 is a diagram showing a single scan field resulting from a scan with the angle $\Phi_o$ equal to zero.
Figure 13B:
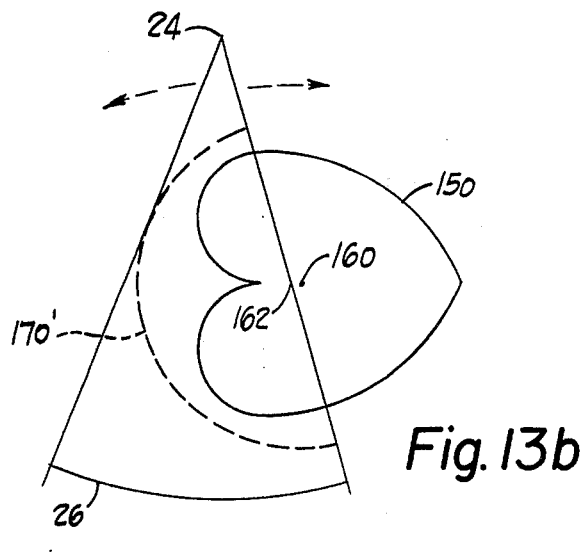
FIGS. 13a–13d are diagrams of an embodiment of offsetting the source-detector assemblies by translation.
Figure 13A:
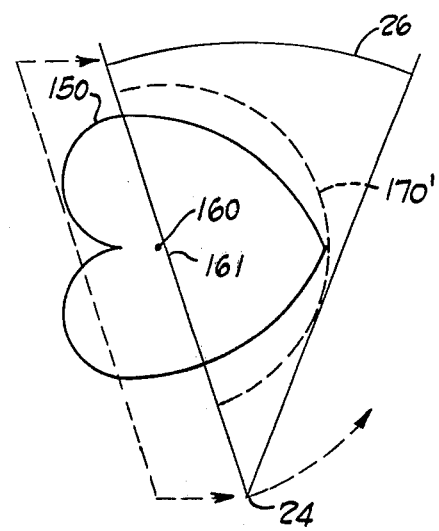
Figure 13C:
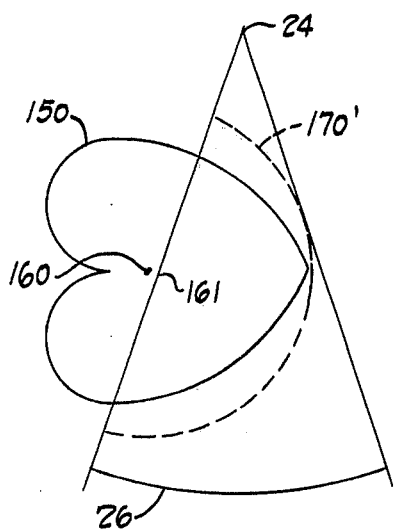
Figure 13D:
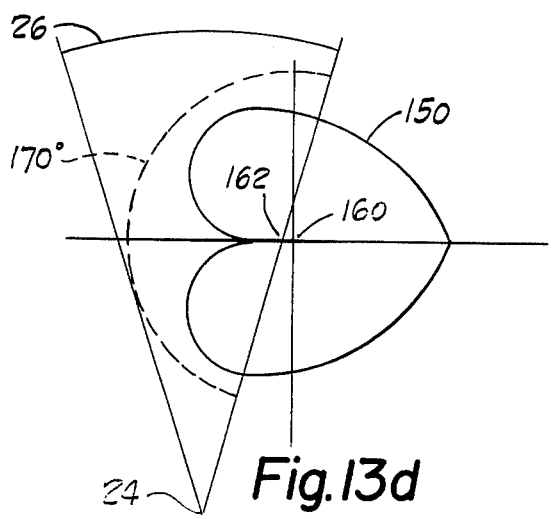
Figure 12A:
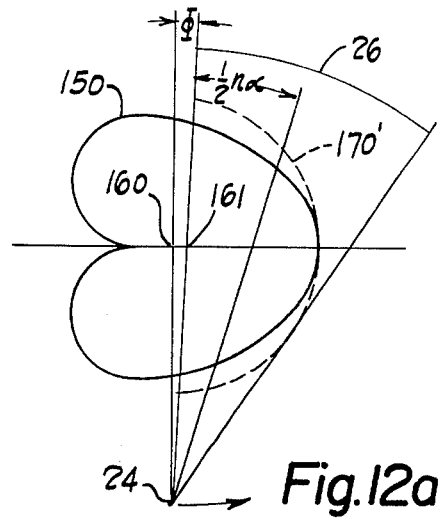
FIGS. 12a–12b are diagrams of a first embodiment of offsetting the source-detector assemblies by rotation.
Figure 12B:
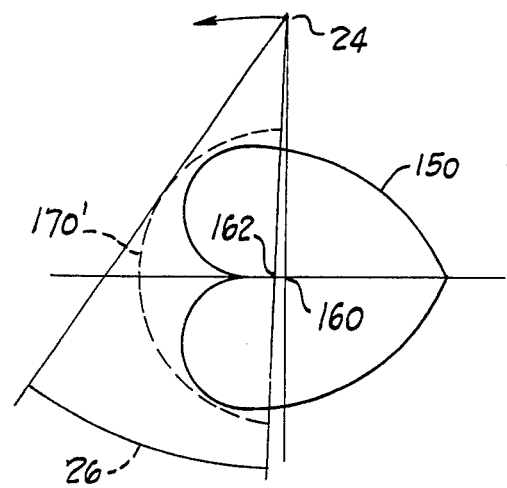

The support structure 28 is generally C-shaped in vertical section and is a yoke 36 rotatively mounted on a stationary support pedestal 38. The source assembly 24 and the detector assembly 26 are rotatably and translatably mounted to source and detector arms 42, 50 of the yoke 36. The arms rotatably support the radiation source and detector assemblies 24, 26 in alignment. Rotation of the yoke 36 effects orbiting of the radiation source assembly 24 and the radiation detector assembly 26 about the patient. The set of X-ray beams are accordingly swept around and through the patient in a plane of orbit which is normal to the system axis 27. In the preferred arrangement the assemblies 24, 26 are movable about a source axis 29 which parallels the system axis 27 and passes through the source arm 42. A pair of stepping motors 62, 64 under the control of the motor control 16 rotate the assemblies about the source axes at a speed of 20° of arc per second. The assemblies are rotated through an initial offset angle and through an incremental angle between successive orbits (respectively referred to as the offset angle $\Phi_o$ and the incremental angle $\Delta \Phi$ in the description accompanying FIG. 10a). During orbiting of the assemblies about the system axis 27, the offset and incremental angles are maintained constant, as will be explained with respect to FIGS. 10–12.

In another embodiment the source and detector assemblies 24, 26 are initially translated each in a direction tangential to its orbital path. The assemblies 24, 26 are then orbited. This embodiment will be explained in detail with respect to FIGS. 13a–13d.

The motor controller 16 comprises conventional circuits for controlling the operation of the stepping motors and for providing encoded data representative of the angular position of output shafts of the stepping motors. Suitable thyristor motor starter and stepping relay control circuits can be selected and coupled to the scanning apparatus 12 to provide the scanning motions according to this invention. Digital shaft encoders 25, preferably of the absolute type, are coupled to the stepping motors for defining absolute angular position of their output shafts. The absolute angular position of the respective output shafts is directly indicative of the amount of rotation about the source and system axes.

The data processor 18 is responsive to the output signals from the radiation detector assembly 26 and to the encoded position data from the shaft encoders 25 for providing a reconstructed image representative of the absorption coefficients in the section of the patient lying in the plane of the source-detector orbit. The processor 18 may be known data processing circuitry utilized in the X-ray transmission scanning technology and will only be described briefly.

The processor 18 comprises a charge integrator/amplifier 30, an analog-to-digital converter 31, an angle sensor 32, a digital storage circuit 33, and a reconstruction processor 34. The integrator amplifier 30 is responsive to the output signals from the radiation detector assembly 26 for providing averaged, analog data signals. The radiation data signals are averaged over a period of time determined (a) according to start and stop signals generated by the angle sensor 32, or (b) from the speed of orbit of the assemblies 24, 26. These data signals have values representing the intensity of the X-ray beam after it has passed through and been attenuated by the patient.

The A/D converter 31 is responsive to the averaged, analog signals and converts them to digital signals. The digital storage 33 is preferably a memory of a digital computer and retrievably stores the digital signals in coordination with the angle sensor 32. More specifically, the angle sensor 32 is responsive to the digital shaft encoders 25 on the apparatus 12 and provides orientation signals indicative of the orientations of the assemblies 24, 26. Values of the orientation signals are compared with a store of predetermined values representing orientations at which measurements are to be taken. In response to the comparison of the sensed values with the stored values, the digital computer either stores the digital signals into predesignated locations, or stores the digital signals into sequential locations and it labels these locations according to the orientation of the assemblies 24, 26.

The digital computer comprising the reconstruction processor 34 is programmed for tomographic reconstruction using any of a variety of known computational processes. Well known computational processes include techniques using filtered back projections, matrix multiplication, and successive appoximations. Reconstruction provides values which, when plotted and displayed, represent radiation absorption or transmission coefficients of the section of the patient scanned. More specifically, the digital signals corresponding to values of absorption at preselected angles of orbit and orientations of the source-detector assemblies 24, 26 are retrieved from the storage 33. These values are processed by the reconstruction processor 34 and are plotted as points of the reconstructed image which are displayed on the display 19.

The yoke member 36 includes an upper support 40 and a lower support 46. The lower support 46 is rotatably mounted on the support pedestal 38 by a shaft 48. The shaft 48 is coaxial with the system axis 27. The lower support 46 is configured in the shape of an L which is swept through an arc such that the detector arm 50 is an arcuate-shaped ledge. The detector arm 50 has arcuate-shaped slots 52 through which the detector assembly 26 is movably mounted via a detector mounting assembly 54.

The upper support member 40 includes the source arm 42. A rotatable pivot bracket 44 is mounted on the source arm 42 for rotation about the source axis. The pivot bracket 44 is coupled via a source mounting assembly 45 to the radiation source assembly 24, FIG. 3. The pivot bracket 44 enables the source assembly 24 to rotate about the source axis through a rotation angle $\phi$ in the plane of the orbit. The rotation angle $\phi$ describes the motion of the source and detector assemblies 24, 26 as they are rotated through the offset angle $\Phi_0$ and through the incremental angle $\Delta\Phi$.

Because a plurality of coplanar beams are used for scanning, the rotational angle $\phi$ is measured from the centerline of the span of the beams, and the angle subtended by the array implements values of the angle $\phi$ without actuation rotation of the assemblies 24, 26 about the source axis. For example, a value of the angle $\phi$ equal to $\pm$ 10° is implemented to a set of beams spanning 20°. Alternatively, a source having a single beam which is swept through 20° about the source axis sweeps an angle $\phi$ of 20°.

The support structure 28 has a plurality of motors for providing the movements of the source and detector assemblies 24, 26. In addition, to the support and detector assembly motors 60, 62, a pivot holder rotating motor 64, a source translating motor 68, and a detector translating motor 70 are provided. All are actuated in response to the motor controller 16. Although not shown, it is understood that the plurality of motors are powered through slip-ring connectors between each motor and the lines 22. Because the slip-ring connectors may be of known construction and do not form a part of the invention, they will not be described in further detail.

Figure 2:
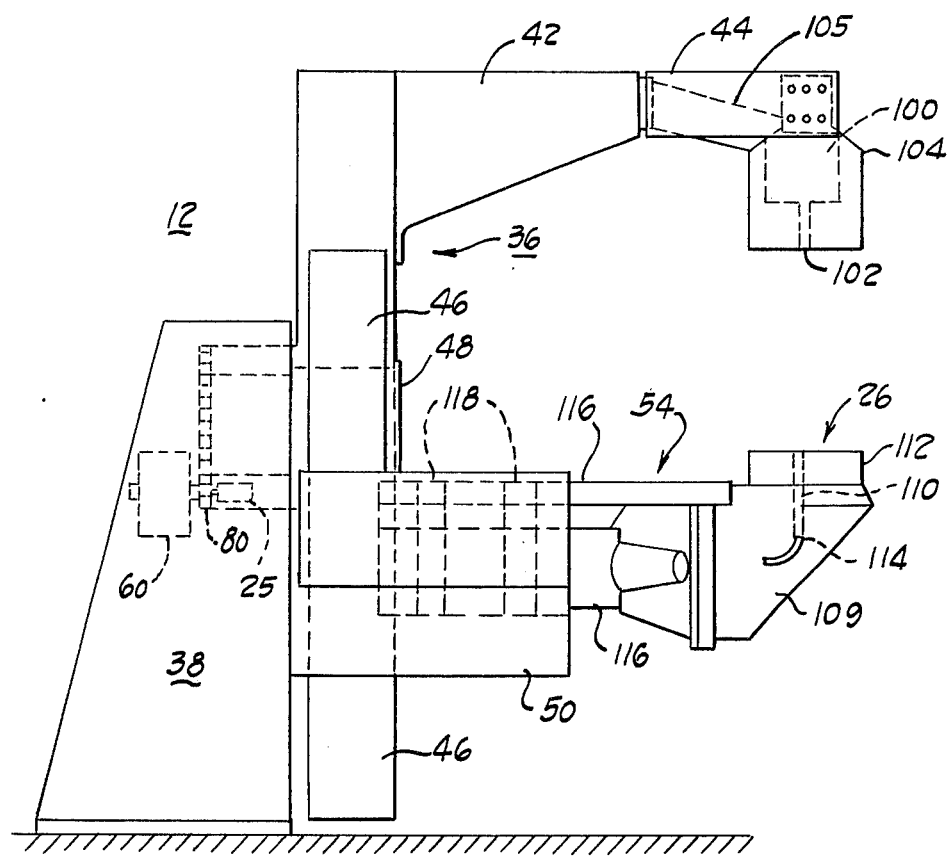
FIG. 2 is a side elevational view of the scanning apparatus of an enlarged scale with respect to FIG. 1.

The support rotating motor 60, FIG. 2, is coupled via linkage 80 to the yoke 36. Actuation of the motor 60 rotates the yoke 36 about the pivot shaft 48 through an angle γ. The rotation of the yoke 36 effectuates orbiting the source-detector assemblies 24, 26 through the angle γ (here referred to as the orbit angle γ) about the system axis 27.

Figure 5:
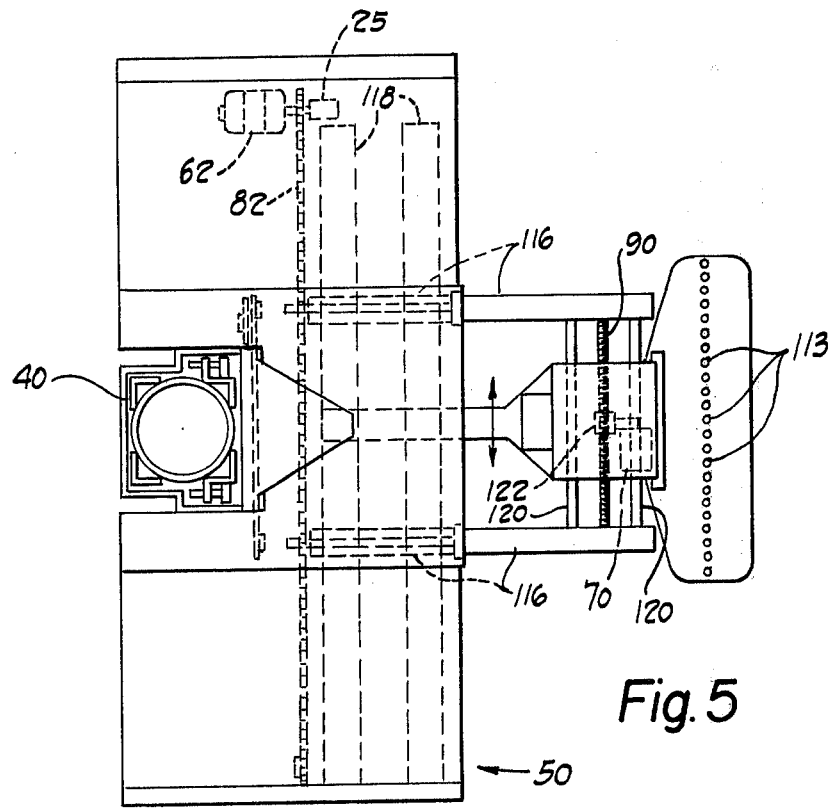
FIG. 5 is a sectional view of the yoke and a plan view of the detector assembly.

The detector assembly rotating motor 62 is shown in FIG. 5 and drives the detector mounting assembly 54 via chain linkage 82. Actuation of the detector assembly rotating motor 62 causes the radiation detection assembly 26 to move in an arcuate path about the source axis 29.

Figure 3:
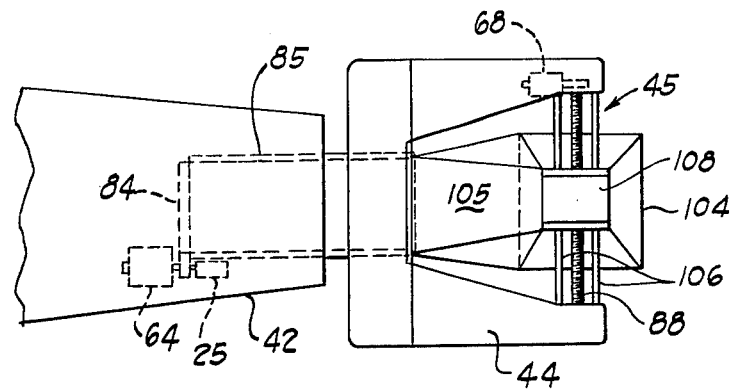
FIG. 3 is a plan view of the yoke and source and detector assemblies.
Figure 4:
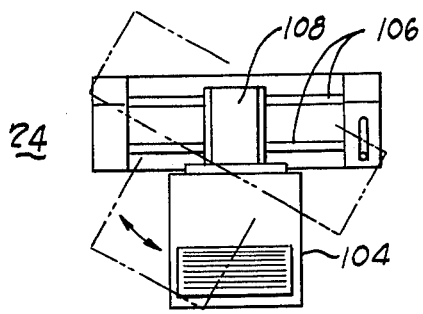
FIG. 4 is a front elevational view of the source assembly.

The pivot rotating motor 64 is shown in FIG. 3 and drives the pivot holder 44 via gear linkage 84 and a hollowed shaft 85 to which the holder 44 is pinioned. Energization of the pivot bracket rotating motor 64 is synchronized with the energization of the detector assembly rotating motor 62 to maintain alignment of the radiation source assembly 24 and the radiation detector assembly 26.

The source translating motor 68 is shown in FIG. 3 and translates the source mounting assembly 45 via a lead screw 88. Energization of the source translating motor 68 causes the radiation source assembly 24 to be translated transversely of the source axis.

The detector translating motor 70 is shown in FIG. 5 and translates the detector mounting assembly 54 via a lead screw 90. The detector translating motor 68 is used to maintain alignment between the source and detector assemblies 24, 26 when the source assembly is translated by the source translating motor and vice versa.

Referring now to FIGS. 2 and 3, a source of X-rays is indicated at 100 and is suitably a 120kv X-ray tube. The tube is in a housing 104 which includes a source collimator assembly 102. A sleeve 105 connects the housing 104 and the hollowed shaft 85 for supporting electrical lines and a cooling system for the X-ray tube. The X-ray tube has a target which provides a conventional cone-shaped emission of radiation. The collimator assembly 102 delineates a plurality of discrete beams which are directed toward the director assembly 26. In a preferred embodiment, the collimator assembly 102 provides twenty collimated beams at angle of separation α, between adjacent beams of 1°. Each beam is collimated to a width on the order of 2–3 mm. which corresponds to a span of approximately 0.2°.

The collimator and the tube target are relatively spaced and configured to provide a beam which approaches truly collimated electromagnetic radiation.

The X-ray tube 100 and its associated electrical connections, cooling jacket, and coolant supply are shown functionally because they may be of known construction and do not form a part of the invention. Suitable X-ray tube assemblies, including the coolant jacket and electrical interconnects, which allow unhindered rotary motion of the X-ray tube as above-described are known, especially in the X-ray tire inspection art. Such assemblies are described in the METHOD and APPARATUS patent applications and in the X-RAY and TIRE patents, which are incorporated by reference.

The source mounting assembly 45 has a pair of support and guide rods 106 and a threaded sleeve 108 which is in threaded engagement with the lead screw 88. The threaded sleeve 108 is slidable along the rods 106 and coupled to the housing 104 of the assembly 24. The support rods 106 are connected to the pivot bracket 44 for supporting the radiation source assembly 24. Actuation of the source translating motor 68 translates the sleeve 108 and thus the source assembly 24 in a direction tangential of the orbital path and in the plane of the orbit.

Referring to FIG. 2, the radiation detector assembly 26 includes a housing 109 which is coupled by the detector mounting assembly 54 to the lower arm 50. The housing 109 encloses a detector collimator assembly 112, sets of scintillation crystals 110, and photomultiplier tubes 114. Each scintillation crystal 110 is preferably calcium fluoride and is interposed between the detector collimator assembly 112 and an associated and optically coupled photomultiplier tube 114. The beams of X-radiation from the source assembly 24 impinge upon the scintillation crystals 110, and scintillations are generated in response to the beams. The scintillations are detected by the photomultiplier tubes 114 which provide electrical output signals having values proportional to the amount of X-radiation received.

The collimator assembly 112 has a number of collimator passages 113 corresponding to the number of passages in the source collimator assembly 102. For the preferred embodiment which utilizes twenty beams of radiation, twenty passages 113 are provided. Axes of adjacent passages are spaced about the source axis by one degree, the angle α, in accordance with the separation of the passages of the source collimator assembly 102. It has been discovered that a one degree spacing between collimator passages reduces the effect of scatter to an acceptable level.

The detector mounting assembly 54 supports the detector assembly 26 for arcuate movement about the source axis and for translational movement along a path which is tangential to the path of arcuate movement. The mounting assembly 54 includes a pair of brackets 116, a pair of support and guide rods 120 and a sleeve 122 which is threadably connected to the beam screw 90. The support and guide rods 120 are connected to the brackets 116 and support the detector assembly 26. The brackets 116 extend through the slots 52 and are coupled to the chain linkage 82. The brackets 116 extend through a pair of guides 118 which are provided in the detector support arm 50. The guides 118 maintain the detector support arm 50. The guides 118 maintain the detector assembly 26 in its arcuate path as it is moved in response to the detector rotating motor 62. The threaded sleeve 122 is coupled to the housing 109 for translating the housing 109 in response to rotation of the lead screw 90.

Figure 14:
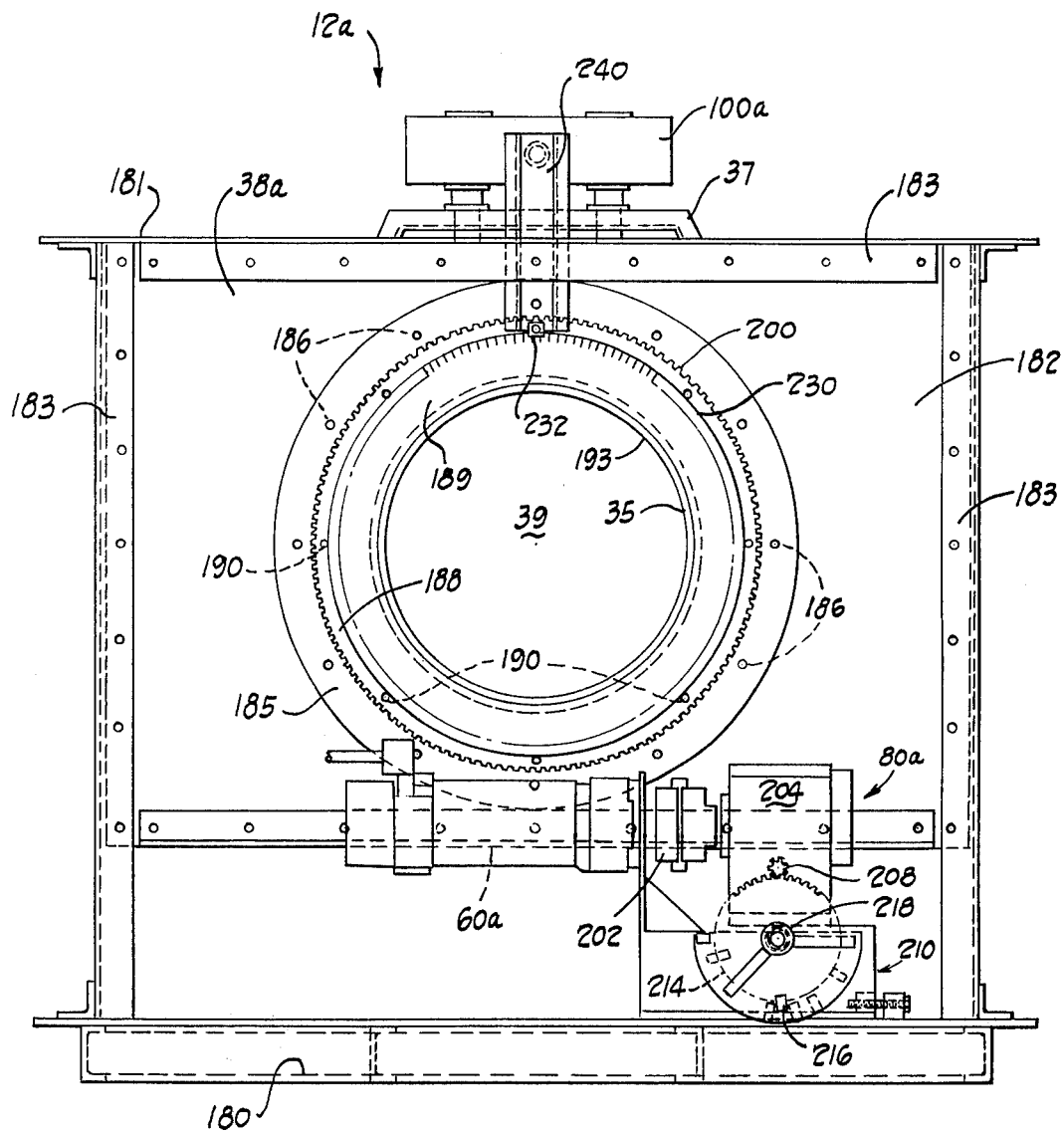
FIGS. 14–17 are diagrams of another scanning apparatus functionally equivalent to that of FIGS. 2–5.
Figure 15:
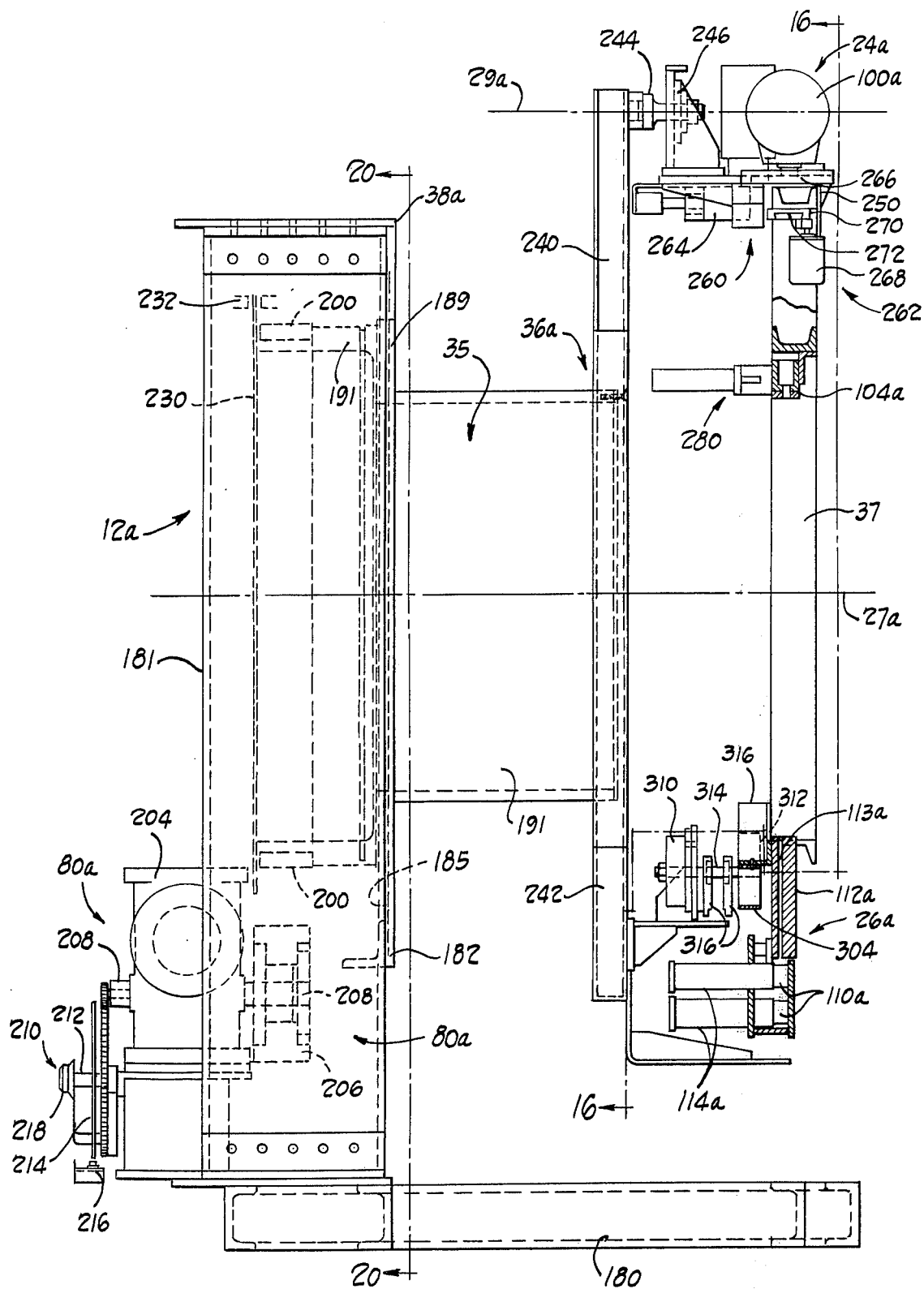
Figure 16:
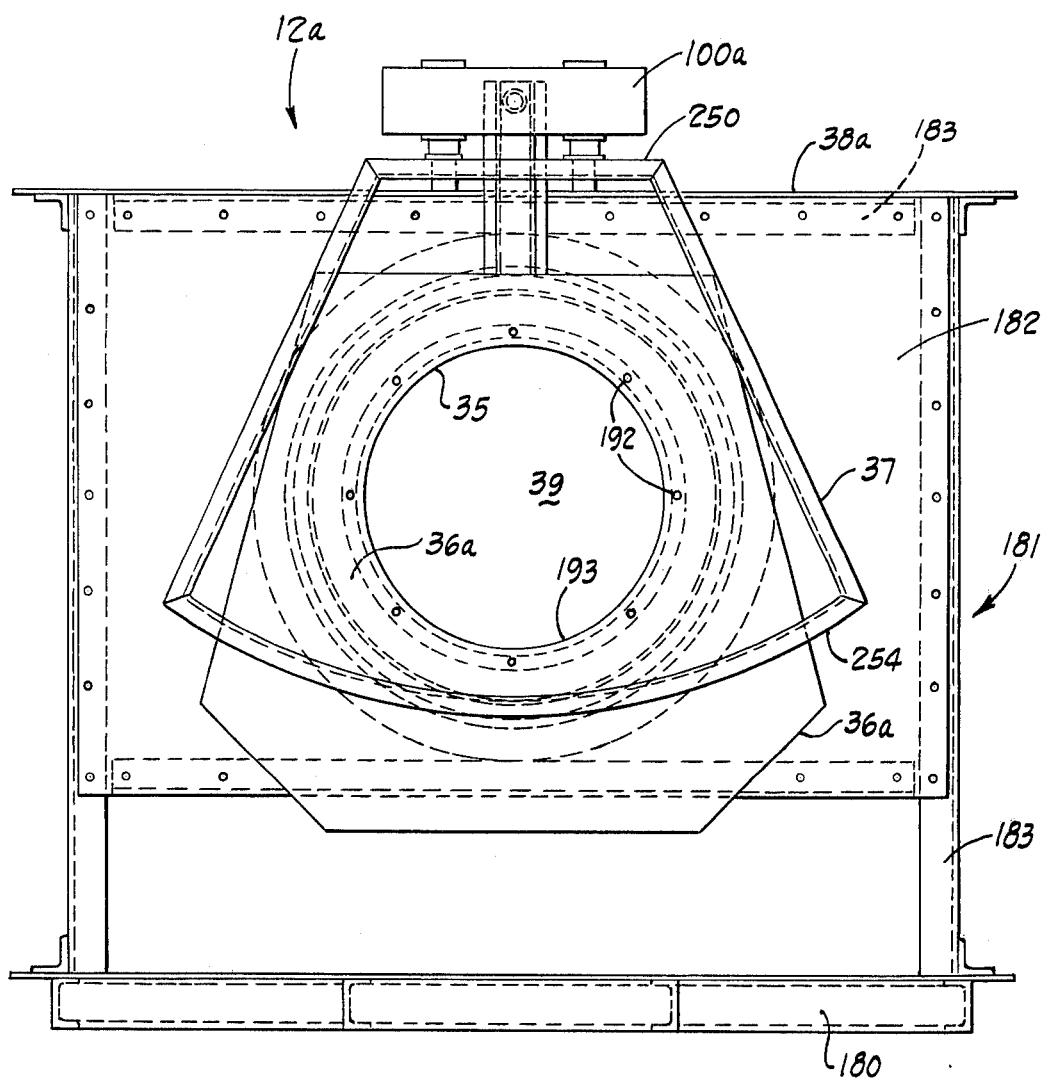

A preferred scanning apparatus is shown generally at 12a in FIGS. 14–16. To minimize duplication of description, certain of the components of the scanning apparatus 12a will be described by the reference numeral of the functionally similar component of the apparatus 12 with the subscript "a" added.

The scanning apparatus 12a includes a rigid main frame 38a. The main frame 38a includes a fabricated base pedestal 180 and an upstanding portion 181 which extends upwardly from a rearward part of the base pedestal 180. The base pedestal 180 extends forwardly of the remainder of the entire scanning apparatus 12a to provide a firm and stable support.

The upstanding portion 181 includes a bearing support plate 182. The bearing support plate is bolted to upstanding and transverse channel members 183 to form a forward face of the upstanding portion 181. The bearing plate 182 includes a machined annular recess 185 which is seen in plan view in FIG. 14. The annular recess 185 provides a mounting surface for a bearing, not shown, which is secured to the bearing plate as by bolting a bearing block to tapped holes 186.

A spindle assembly 35 is journaled in the bearing. The spindle assembly 35 includes a relatively large diameter journaling tube 188. The journaling tube 188 is secured to a flange portion 189 of the spindle assembly 35 as by bolts 190. The flange portion 189, in turn, is welded to a forwardly extending mounting sleeve 181. The mounting sleeve 181 extends forwardly through an aperature in the bearing support plate 182.

A rigid frame 36a known as an oscillatory frame is fixed to the forward end (to the right as viewed in FIG. 15) of the mounting sleeve 191 as by bolts 192, FIG. 16. The oscillatory frame 36a has an aperture 193 of slightly reduced diameter with respect to the inside diameter of the sleeve 181. The oscillatory frame aperture 193 and the spindle assembly 35 are axially aligned along a system axis 27a.

The oscillatory frame 36a includes an upstanding neck portion 240. A pivot pin 244 is supported to the neck portion 240 near its top, FIG. 15. A delta-shaped frame, 37 (as viewed in FIG. 16) is pivotally supported on the pivot pin 244 for rotation about the axis of the pivot pin 244, which axis is a source axis 29a.

An X-ray source assembly 24a and a detector assembly 26a are fixed in alignment to the delta frame 37 for movement with the delta frame 37 as a unit about the source axis 29a. The pivoting of the delta frame 37 about the source axis 29a is initially accomplished during setup. Once the delta frame 37 has been positioned in a desired and selected location, the delta frame, the supported source and detector assemblies 24a, 26a, the oscillatory frame 36a and the spindle assembly 35 all are rotated as a unit about the system axis 27a. This rotation about the system axis 27a orbits the source and detector assemblies 24a, 26a about a patient for effecting X-ray studies. After the assemblies 24a, 26a have completed an orbit, the delta frame 37 may be incrementally pivoted in preparation for another orbiting. When the system is in use, a fixed, large-diameter tube (not shown) extends through the spindle assembly 35 and the oscillatory frame 36a. This tube protects the patient, positioned partly within a central aperture (indicated at 39) of the spindle assembly 35, from the rotating spindle assembly.

The orbital motion of the assemblies 24a, 26a defines the rotation angle $\phi$ as described with respect to the scanning apparatus 12. The pivoting of the assemblies 24a, 26a about the source axis 29a define an initial offset angle and an incremental angle between successive orbits (respectively referred to as the offset angle $\Phi_o$ and the incremental angle $\Delta\Phi$ in the description accompanying FIG. 10a). During orbiting of the assemblies about the system axis 27a, the offset and incremental angles are maintained constant, as is explained with respect to FIGS. 10–12.

To effect orbiting of the assemblies 24a, 26a, the spindle assembly 35 carries a pulley 200. Linkage 80a couples the pulley 200 to a spindle drive motor 60a for effecting rotation of the spindle assembly 35.

Referring to FIG. 14 the linkage 80a includes a torque limiting coupler 202 and a transmission 204a which are coupled to the spindle drive motor 60a. The transmission 204 has its output shaft 206 carrying a pulley 208 (FIG. 15). A drive belt (not shown) is carried by the pulleys 200, 208 to allow operation of the spindle drive motor 60a to rotate the spindle assembly 35.

The spindle drive motor 60a is a permanent magnet, D.C. servo-motor which allows reversible output operation. The motor 60a has an automatic brake which is automatically applied unless drive power is supplied to the motor 60a. The motor 60a is operated to rotate the spindle assembly 35 through a predetermined number of degrees, to come to a soft stop, and finally to reverse directions, if so programmed, to allow multi-orbit scans of the source/detector assemblies 24a, 26a.

To this end, the transmission 204 has a limit switch assembly 210 coupled to the output shaft 206. The switch assembly 210 includes a reduction shaft 212 which is geared, by associated pulleys on it and on the output shaft 206, to operate at ½ the rotational rate of the output shaft 206. The reduction shaft 212 carries a timing disc 214 having a pair of timing markers (not shown). The timing markers travel less than a full rotation even though the output shaft 206 has travelled up to one-and-three-quarters revolutions during scanning of the assemblies 24a, 26a.

The limit switch assembly 210 also includes a potentiometer 218 and a photodiode detector 216 positioned for monitoring the timing markers. The detector 216 monitors rotation of the timing disc 214 and, upon detection of the timing markers, produces signals which break the spindle driving motor 60a and cause the motor 60a to reverse direction if multi-orbit studies are scheduled. The potentiometer 218 is mounted to the reduction shaft 212 for producing an analog signal which is indicative of the actual orientation of the spindle assembly 35 from a zero degree reference. This signal is indicative of the orbital angle $\gamma$ and is coupled to the angle sensor 32.

In order that the radiation impinging upon the detector assembly 26a may be averaged over an integration interval corresponding to rotation of the spindle 35, a spindle timing disc 230 is attached to the spindle 35. In the illustrated embodiment, the timing disc 230 is attached to the end of the spindle 35 which carries the spindle pulley 200. The spindle timing disc 230 has indicia corresponding to subdivisions of degrees.

A spindle diode detector is illustrated schematically at 232 and is positioned for monitoring the indicia on the spindle timing disc 230. The spindle diode detector 232 generates a series of pulses corresponding to the subdivisions of degree indicia passing adjacent the detector during rotation of the spindle 35. These pulses are coupled to the charge integrator/amplifier 30 for use in defining a particular integration interval over which the radiation intensity is average.

The oscillatory frame 36a defines a mounting surface 242 diametrically opposite the neck portion 240. A support assembly is secured to the oscillatory frame mounting surface 242 and includes pairs of support rollers 243 which define guides for the delta frame 37.

The delta frame 37 includes a source mounting member 250 which is pivotally coupled to the pin 244 by a bracket 252. The frame 37 also includes an arcuate-shaped member 254 diametrically opposite the source mounting member 250 about the passageway 39. The radiation source assembly 24a is mounted to the source mounting member 250 for directing beams of radiation transversely of the passageway 39 (radially of the source axis 29a).

The side elevational view shown by FIG. 15 depicts part of the delta frame 37 below the member 250 and other adjoining apparatus in cross-section. It is further noted in FIG. 15 that for convenience of illustration some of the apparatus adjoining the cross-sectioning has been removed from the view.

Figure 17:
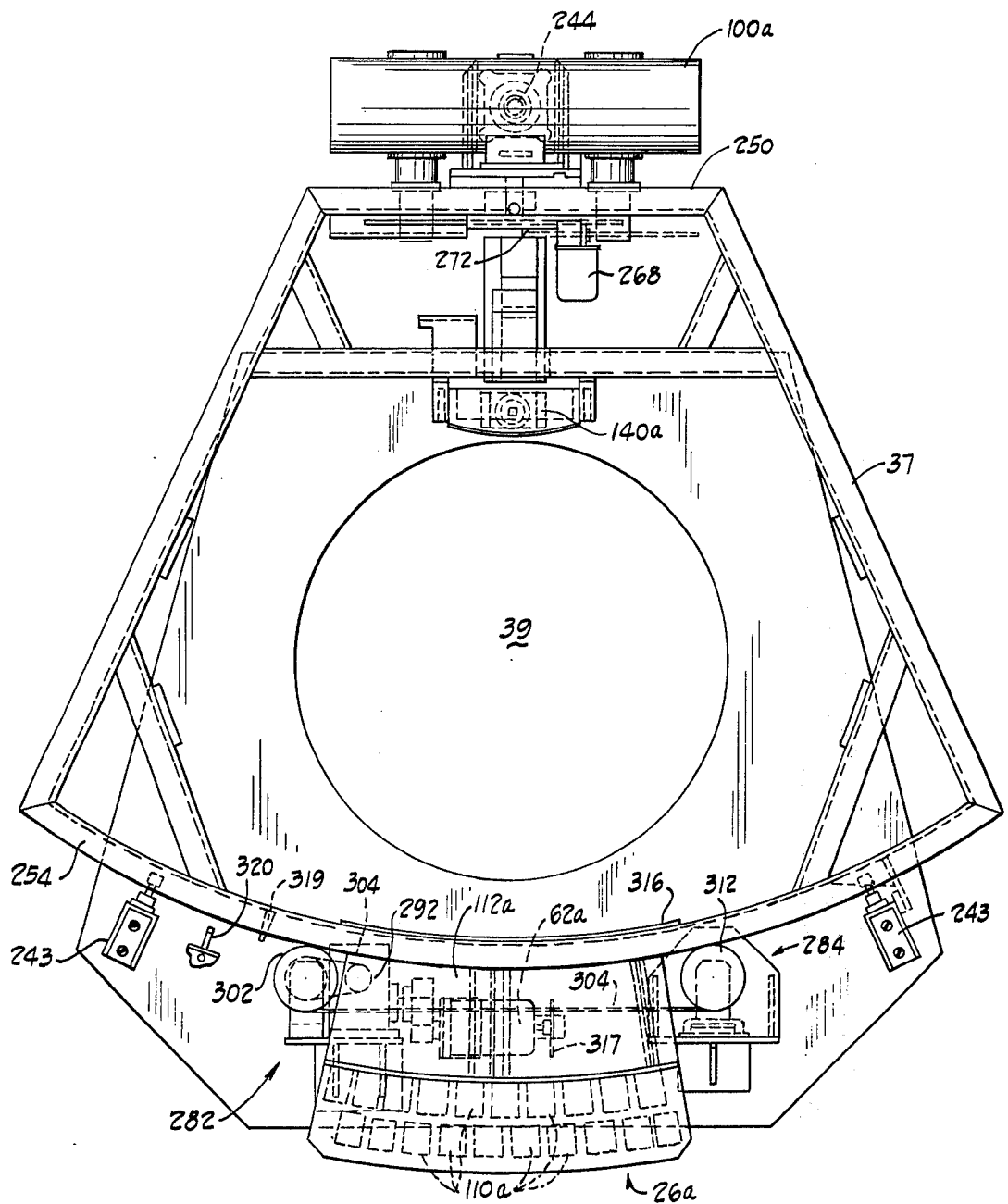

The delta frame 37 is driven about the source axis 29a (defining the angle $\phi$) by a drive arrangement 282 which is mounted on the oscillatory frame mounting surface 242. Referring additionally to FIGS. 17–19, the drive arrangement 282 includes a stepping motor 62a, its associated linkage 82a to the delta frame 37, and an electronically actuated braking assembly 284.

The design of the linkage 82a is an advantageous feature as it allows the stepping motor 62a to be operated to provide a wide choice of increments for the source/detector assemblies 24a, 26a when they are rotated about the source axis 29a during multi-orbit scans. The linkage 82a is designed with respect to the stepping motor 62a to provide 240 steps or increments per degree of rotation of the source/detector assemblies 24a, 26a about the source axis 29. The selection of the value of 240 steps per degree is a feature in that it provides increments of rotation about the source axis 29a (increments of the rotation angle $\phi$) which are fractional multiples of degrees. This value is especially convenient for accommodating studies which require differing number of orbital scans of the assemblies 24a, 26a. For example, the illustrated scanning apparatus 12a has adjacent detectors spearated by an angle $\alpha$ of 1°. Two hundred forty steps per degree provides a wide range of a rational number subdivisions of this spacing which are necessary for the proper incrementing and initial affect of the assemblies 24a, 26a, about the source axis 29a (defining the angles $\Delta\Phi, \Phi_o$ respectively) for multi-orbit scans. 240 steps per degree also allows a wide range of fractional multiples of other spacings between adjacent detectors 26a for providing the proper incrementing and offsetting of the assemblies 24a, 26a about the source axis 29a.

Referring to FIGS. 17–19, the stepping motor 62a is a conventional stepping motor having 200 steps per revolution. The linkage 82a coverts this motion into the desired 240 steps per degree motion.

The linkage 82a includes a 14 tooth, 3/8 pitch sprocket 290 coupled to the output shaft of the stepping motor 62a. A 7.5:1 ratioed gear reducer 292 is provided. The gear reducer 292 is coupled by a 22 tooth, ⅜ths pitch sprocket 294 tooth sprocket 290. This arrangement establishes 1.57:1 ratio between the stepping motor 62 and the gear reducer 292.

A 14 tooth, ⅜ths pitch sprocket 296 is connected to the output of the gear reducer 292 and interfaces with a 22 tooth, ⅜ths pitch sprocket 298. This arrangement provides a 1.43:1 ratio between the gear reducer 292 and the sprocket 298.

An output sprocket 302 is connected by a shaft 300 to the sprocket 298. The output sprocket 302 is a 22 tooth, 0.187 pitch, 35mm sprocket which is suited for accommodating a 35mm stainless steel drive band 304. The band 304 connects the output sprocket 302 to the braking assembly 284.

Referring to FIG. 15, the braking assembly 284 includes a clutch mechanism 310 which is coupled to the metal belt pulley 312 by a shaft 314. The shaft 314 is rotatably secured within a bracket 316 which is attached to the oscillatory frame mounting surface 242. The belt pulley 312 receives the drive band 304, and the assembly 284 brakes motion of the drive band 304 unless the clutch mechanism 310 is actuated, i.e., whenever the delta frame 37 is to be rotated about the source axis 29a. Limit switches (not shown) are provided on the delta frame 37 for deactuating the clutch mechanism 310 and applying the brake whenever overtravel of the delta frame 37 is detected.

An arcuate-shaped bar 316 of the same arcuate shape as the arcuate-shaped member 254 of the delta frame 37 is secured to the member 254. The band 304 is reeved around the output sprocket 302 and the pulley 312 and has its ends fastened to the bar 316. Accordingly, as the stepping motor 62a advances the band 304, the delta frame 37 is advanced.

The tops of the output sprocket 302 and the pulley 312 are adjacent the outer side (i.e., the convex side) of the bar 316 and are circumferentially spaced from the connection of the bar 316 and the band 304. This configuration is a feature of the linkage 82a as it allows the band 304 to conform to the arcuate shape of the bar 316 and to depart tangentially of the bar 316 as it reeves around the output sprocket 302 and around the pulley 312. This allows the advancing of the band 304 to advance the delta frame 37 the same amount regardless of the orientation of the source/detector assemblies 24a, 26a, about the source axis 29a. More specifically, a one-centimeter advance of the band 304 will always cause a one-centimeter linear advance of a point on the member 254. This linearity facilitates accurate incrementing of the assemblies 24a, 26a about the source axis 29a when an increment in the rotational angle $\phi$ is required between orbital scans.

In order to measure the orientation of the assemblies 24a, 26a about the source axis 29a, the stepping motor 62a is equipped with a timing disc 317 having timing markings on it. A photodiode detector 318 is positioned for monitoring the marking and for producing another one of the READ signals to the angle sensor 32. This READ signal conveys the value of the rotation angle $\phi$.

In order to detect when there is no offset of the assemblies 24a, 26a about the source axis 29a (i.e., when there is no offset in the $\phi$ direction), an indicator 319 and another detector 320 are provided. Whenever the indicator 319 is advanced in alignment with the detector 320, the indicator generates a signal representing that there is no offset of the assemblies 24a, 26a in the $\phi$ direction.

The source assembly 24a includes an X-ray tube 100a, a fail-safe shutter mechanism 260, and a filter mechanism 262. The shutter mechanism 260 includes a spring loaded solenoid 264 and a radiation blocking shutter 266. The solenoid 264 is actuated during scanning of the assemblies 24a, 26a to withdraw the shutter 266 from the path of the X-ray beam.

The filter mechanism 262 includes a filter drive motor 268 which drives a rack 270. The rack 270 carries a plurality of metal filters which are respectively positioned within the path of the X-ray beam to attenuate frequencies of the X-ray beam in a band pass fashion.

As a feature, the X-ray tube 100a is mounted such that its X-ray tube target is mounted in axial alignment with the pin 244 and thus is mounted in coincidence with the source axis 29a. This allows the focal spot of the radiation to lie on the source axis 29a regardless of the orientation of the delta frame 37 about the source axis 29a.

Primary and secondary collimators 104a, 112a are secured to the delta frame 37 at positions spaced diametrically about the passageway 39 and in alignment with the X-ray tube 100a. The primary collimator 104a delineates the beam of radiation into a plurality of coplanar beams separated by an angle $\alpha$ and emanating from the target of the X-ray tube 100a. The secondary collimator 112a minimizes scatter radiation.

The detector assembly 26a is connected to the arcuately-shaped member 254 and in axial alignment with the collimators 104a, 112a for receiving the collimated beams of radiation. The detector assembly 26a includes a plurality of detectors each including a radiation sensitive detector crystal 110a and an associated photomultiplier tube 114a. *The photomultiplier tubes 114a, although the connections are not shown, are connected to the integrator amplifier 30 shown in FIG. 1.*

The detectors are mounted in first and second arcuate-shaped concentric rows about the source axis 29a. The orientations of the first and second rows about the system axis 29a are relatively offset, and adjacent detectors of each row are spaced by an angle $2\alpha$ such that adjacent beams of radiation impinge on detectors in different rows. This arrangement allows a greater number of individual detectors to be placed within the fan beam of X-radiation since otherwise the finite size of each individual detector would limit the number of detectors positionable within the fan-shaped beam.

A reference channel detector assembly 280 is also connected to the delta frame 37. It is offset from the plane established by the axes of the beams of radiation, and is positioned for receiving a reference beam of radiation produced by the X-ray tube 100a. The reference channel assembly 280 is constructed similarly to the respective detectors in the detector assembly 26a, and is used for monitoring the output consistency of the X-ray tube 100a.

A plurality of conductors must be coupled to the source/detector assemblies 24a, 26a. For example, control lines, high voltage power lines, and oil coolant passages are coupled to the X-ray tube 100a; control and power lines are coupled to the filter drive motor 68; control lines are coupled to the solenoid 264; and signal lines are coupled to the detector assemblies 26a. These conductors are bundled as a cable 321.

To accommodate rotation of the source/detector assemblies 24a, 26a, a cable take-up mechanism 322 is provided. As is shown in FIG. 20 the cable take-up mechanism 322 includes a plurality of four cable supporting drums 323, 324, 325, 326. The drums 324, 325 are stationarily mounted to the main frame as idlers 38a, and the drums 323, 326 are slidably mounted on respective shafts 330, 332 for taking up any slack in the cable 321.

The cable 321 is clamped at a position 334 on the main frame 38a and is reeved over the slidably mounted drum 323. From the drum 323 the cable is routed over the stationary drums 324, 325 and is reeved around the other slidably mounted drum 326. From the drum 326 the cable is secured to the spindle 35 and is routed from there to the source/detector assembly 24a, 26a. As the spindle 35 rotates, the cable winds and unwinds from the spindle 35, and the movable drums 323, 326 advance on the shafts 330, 332 for taking up any excess cable.

Although for many applications the weight of the drums is sufficient to take up the excess cable, high speed operation has been improved through the use of a spring actuated retractor 336 coupled to the moving drum 323. The retractor 336 urges the slidably mounted drum 323 away from the clamped position 334 whenever there is an excess of the cable 321.

The Computational Process

The preferred method of using filtered back projections to reconstruct a tomographic image is based on Equation 1 below. This equation is similar to that found in Sweeney, "Interferometric Measurement of Three Dimensional Temperature," PhD Thesis, University of Michigan, 1972.

$$A(x,y) = (\pi/N_\theta) \sum_{n=1}^{N_\theta} f(x \cos \theta_n + y \sin \theta_n, \theta_n), \quad (1)$$

where i. $A(x,y)$ is the reconstructed, or estimated, value of a desired absorption density $a(x,y)$ at the point $(x,y)$. The estimate is to be evaluated at a discrete set of reconstruction points $(x_1, y_1), (x_2, y_2), \ldots$ in the $(x,y)$ plane.

ii. $f(x \cos \theta + y \sin \theta, \theta) = f(t,\theta)$ which is a polar coordinate function of the translation variable t determined from the measurements $m(t,\theta)$ at an angle $\theta$ lying within a plane passing through the patient according to $$f(t,\theta) = \int_{-\infty}^{\infty} h(t-\tau)m(\tau,\theta) \, d\tau, \quad (2)$$

where $h(t)$ is the filter impulse-response required for reconstructive tomography.

iii. $N_\theta$ is the number of angles at which data are collected, where $$\theta_n = \pi n/N_\theta \text{ for } n = 0,1 \ldots, (N_\theta - 1).$$

In practice, the continuous sum or integral in (2) is replaced by a discrete sum of the form $$f(t,\theta) = \sum_{K=1}^{N_t} h(t-\tau_k)m(\tau_k,\theta)\Delta\tau, \quad (3)$$

where $N_t$ is the number of translation positions where measurements are made.

Detailed descriptions of and comparisons of the various computational processes are found in Cho, *Generalized Views* on *3-D Image Reconstruction and Computerized Transverse Axial Tomography*, IEEE Transactions on Nuclear Science, Vol. NS-21, June, 1974.

The operation of the tomographic system 10 for generating the function $f(t,\theta)$ is best understood when considering FIGS. 6–9. FIG. 6a illustrates a hypothetical cross-section 150 of a specimen under study. Its interior points are denoted in polar coordinates as $(t_k,\theta_n)$ about an origin 160 lying within the plane of the cross-section.

Figure 6B:
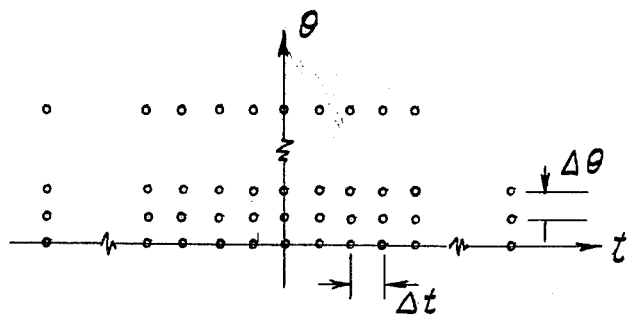
FIG. 6b is a plot of the measurement points in the coordinate system of FIG. 6a at which intensity measurements are plotted for exact image reconstruction.
Figure 6A:
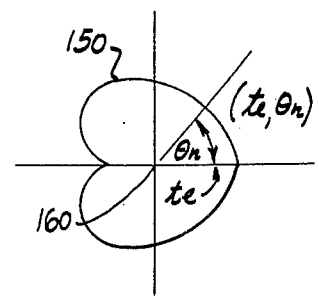
FIG. 6a is a diagrammatic presentation of a polar coordinate system about a center of orbit lying in a cross-sectional plane of the patient.

FIG. 6b depicts a set of measurement points $m(t_k, \theta_n)$ substantially uniformly spaced in the $(\theta, t)$ plane. Radiation intensity measurements taken at these points, or sufficiently near these points to render accurate interpolations provide exact reconstruction of the cross-section lying in the $(\theta, t)$ plane.

For measurements that are spaced uniformly in the $(\theta, t)$ coordinate system at points indexed by $k$ and $n$ $$t(k) = k(\Delta t), k \in \left\{ \frac{t_{min}}{\Delta t}, \ldots, \frac{t_{max}}{\Delta t} \right\}$$

$$\theta(n) = n\Delta\theta, n \in \left\{ 0, \ldots, (\pi/\Delta\theta) - 1 \right\}$$

we have a total of $[(t_{max} - t_{min})(\pi)] / [(\Delta t)(\Delta\theta)]$ measurement points. To satisfy Equation 2 for generating the measurement points $m(t_k, \theta_n)$ in FIG. 6b the measurements must be taken at $k = 1, 2, \ldots N_t$ and $n = 0, 1, \ldots, (n_\theta - 1)$.

The increments $\Delta\theta, \Delta t$ are chosen in accordance with the degree of resolution desired in the reconstructed image. For example, higher resolution may be required in a brain study than in a liver study.

Figure 7A:
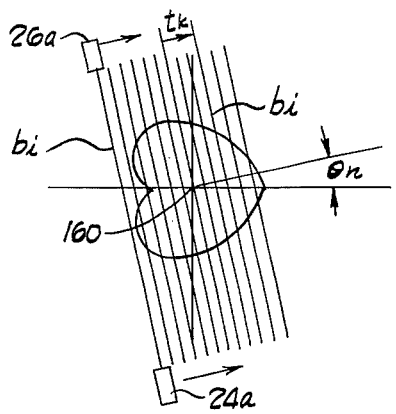
FIG. 7a is a functional representation of a conventional scanning technique which scans the measurement points of FIG. 6b.

One scanning technique which has been developed for generating the required data for reconstruction at the measurement points $m(t_k, \theta_n)$ is shown in FIG. 7a. This technique is the rectilinear scanning technique described in the prior art section of this application and in the reference Cho publication. A radiation source 24a directs a beam of radiation, b, to radiation detector 26a. The source-detector pair 24a, 26a are rotatably and translatably held in spaced alignment. The pair 24a, 26a are translated at a selected orientation, $\theta$, about the origin 160 (which is shown for convenience as coincident with the center of orbit) and a plurality of measurements are taken. At the completion of the translational scan, the source-detector pair 24a, 26a is rotated to a different angle $\theta$ and again is rectilinearly translated with measurements taken at the same translational values $t$.

The rectilinear scanning techniques of FIG. 7a measures data at one of the measurement points $m(t_k, \theta_n)$ for each measurement during a translational scan. Therefore one translational scan generates one row of measurement points in FIG. 6b.

Figure 7B:
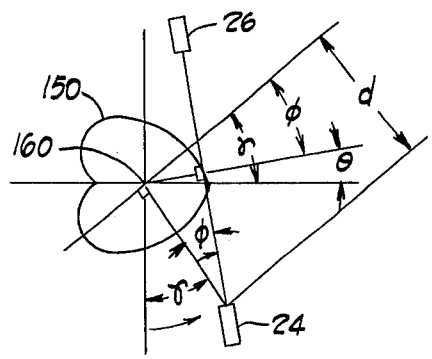
FIG. 7b is a functional representation of a compound axial scanning technique according to the invention which scans the measurement points of FIG. 6b.

As earlier noted this rectilinear scanning technique requires acceleration, deceleration and direction reversals of the source-detector pair 24a, 26a at the end of each translational scan prior to rotation of the source-detector pair about the origin 160 to provide a new angle $\theta$. The acceleration, deceleration and direction reversal requirements of a source-detector pair of typically large mass limits the speed with which the necessary data can be collected. If 180 scans of the specimen are scheduled, a total of 179 direction reversals, accelerations, and decelerations must be accomplished for complete reconstruction. Not only is an unduly massive system requisite for accommodating these translational movements, but the large number of movements are also unnecessarily time-consuming. FIG. 7b depicts a compound angular scanning motion which provides the necessary orientations of the beam for taking measurements at the measurement points $m(t_k, \theta_n)$ of FIG. 6b. FIG. 7b illustrates the compound axial scanning movement of the system 10 of FIG. 1 which allows reduction of the number of required accelerations, decelerations and direction reversals of the assemblies 24, 26 when used according to this invention. The source-detector assemblies 24, 26 are rotatable as a unit in the orbital plane which contains the cross-sectional of the specimen 150. The assemblies 24, 26 rotate about the source axis which is orthogonal to the cross-sectional plane and which is orbited about the origin 160. It is understood that the center of orbit and the origin 160 are chosen coincident for simplifying description. The axially moving pair 24, 26 provides a set of beams in the cross-sectional plane which scans the specimen 150 in a plurality of orientations. Orbiting the source-detector pair 24, 26 about the origin 160 defines the orbit angle $\gamma$. Rotation of the source-detector pair 24, 26 about the source axis defines the rotation angle $\phi$.

As noted above the measurement points $m(t_k, \theta_n)$, depicted in FIG. 6b may be scanned using the compound angular scanning arrangement of FIG. 7b which may be implemented using the system 10 of FIG. 1. The measurement at the angle of rotation $\phi$ of clockwise rotation around the source pivot and the orbit angle of counter-clockwise rotation around the origin is identical to the measurement at points $m(t_k, \theta_n)$ at $t_k$ and $\theta_n$ in the original coordinate system with $t = d \sin \phi$ and $\theta = \gamma - \phi$, where $d$ is the distance of the source axis to the origin.

To acquire the same data in the new geometry, measurements must be made at $$\phi(k) = \sin^{-1} \frac{k\Delta t}{d} = \sin^{-1}\left(\frac{t_k}{d}\right) \quad (4)$$

and $$\gamma(k,n) = n\Delta\theta + \sin^{-1} \frac{k\Delta t}{d} = n\Delta\theta + \sin^{-1}\left(\frac{t_k}{d}\right) \quad (5)$$

For small values of the angle $\phi$, EQUATIONS (4) and (5) simplify to $$\phi(k) = \frac{k\Delta t}{d} \quad (6)$$

$$\gamma(k,n) = n\Delta\theta + \frac{k\Delta t}{d} \quad (7)$$

A variety of compound angular scan motions are effective for either scanning the beam from the source 24 through the measurement points of FIG. 6b or sufficiently near the measurement points to provide the desired degree of accuracy in reconstruction. More specifically, the scanning paths, as will be described, may be designed to pass through the measurement points exactly, or they may be designed to pass proximate to the reconstruction points to allow an interpolation of the detected intensity to approximate a beam passing through the point. If less accuracy is acceptable, the step of interpolation may be eliminated. All such described paths will be referred to as passing through the measurement points.

Figure 8:
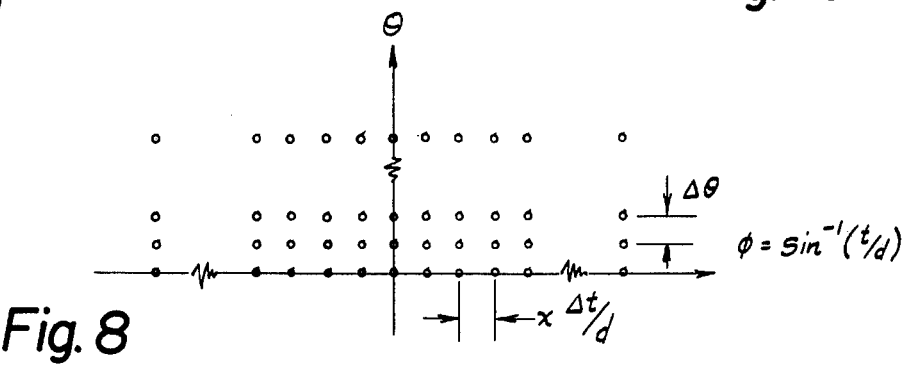
FIG. 8 is a graph of the measurement points of FIG. 6b replotted in terms of compound angular motions $\theta$, $\phi$.

To facilitate understanding of the relationship between the scanning angles $\phi$, $\gamma$ to the measurement points, $m(t_k, \theta_n)$ in FIG. 6b, the points are replotted as functions of $(\theta, \phi)$ in FIG. 8. The plot of FIG. 8 assists in understanding the preferred compound axial scanning mode having nonconcurrent axial motion about the source and system axes.

As seen in FIG. 8 the measurement points $m(t_k, \theta_n)$ generally replot as an array of points in $(\theta, \phi)$ having rows parallel to the $\phi$ axis. The points appear as substantially evenly spaced points in the $\phi$ direction for small values of the angle $\phi$. This is a reasonable approximation in the preferred scanning embodiment as the angle of rotation $\phi$ is generally limited to a relatively small range, such as $\pm 10°$. More specifically, the X-ray source 100 (FIG. 2) provides a fan-shaped beam spanning 20°. Because the angle $\phi$ is defined from the center of the array of detectors when used with a fan-shaped beam, the beam spans an angle $\phi$ of rotation of $\pm 10°$. The approximation that $\sin \phi = \phi$ for small values of $\phi$ therefore holds.

The simplification resulting from assuming the value of the angle $\phi$ to be measured from the center of the array is for ease of description. It will be understood that each beam/detector pair in the N detector array introduces an angular modification of the value of the angle $\phi$. For example, the beam/detector pair which is "$i$" beams away from the center measures intensity at the angle $\phi + i\alpha$, depending on which side of the center the $i$ th beam is.

Compound angular scanning utilizes either nonconcurrent or concurrent angular motions. The preferred embodiment of nonconcurrent, $\phi$ and $\gamma$ angular motion about the origin 160 and about the source axis is explained with respect to FIGS. 9a–9c. The $\phi$ scanning motions is held constant for each orbit, and X-ray intensity measurements are taken to satisfy the angular relationships $\phi = \sin t_k/d$; $\gamma - \phi_k = \theta$.

Figure 9A:
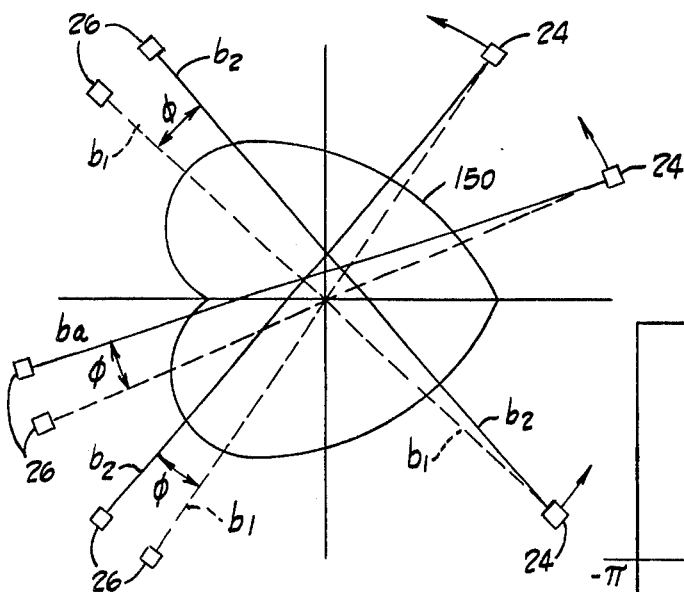
FIG. 9a–c are diagrams which illustrate operation of the tomographic system of FIG. 1 to provide nonconcurrent compound axial scanning motions.
Figure 9B:
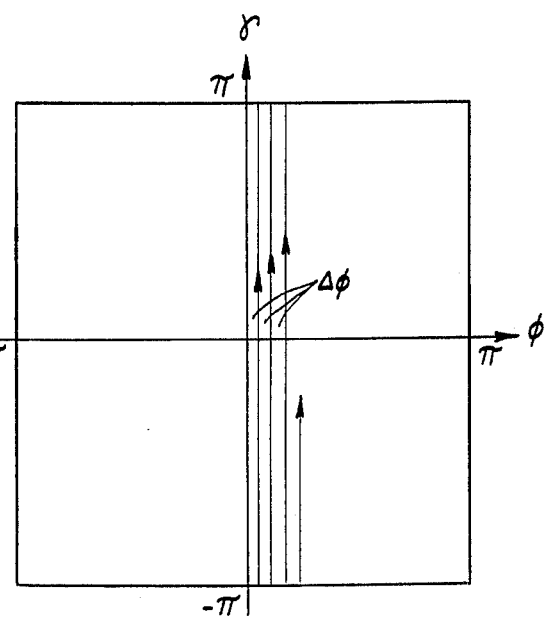
Figure 9C:
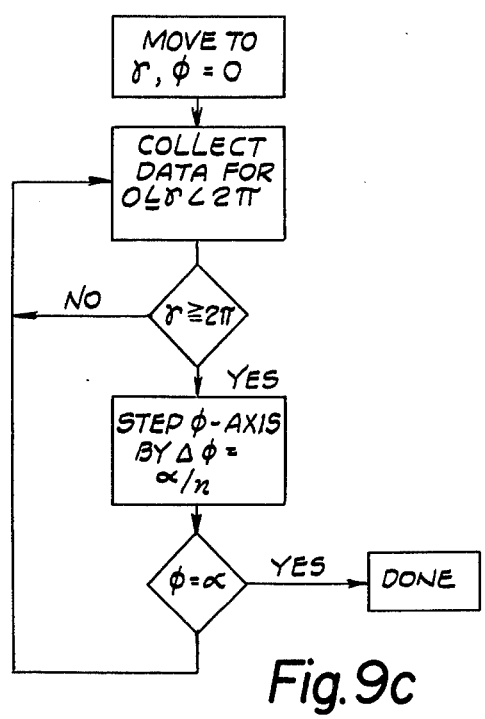

The preferred scanning embodiment for the system 10 utilizes nonconcurrent $\phi$, $\gamma$ angular scanning motions and is illustrated in FIGS. 9a–c. FIG. 9a illustrates a complete orbital scan of approximately 360° (providing beam b2) in conjunction with a hypothetical orbital scan providing beam b1 passing the origin. FIG. 9b represents a plot of the scan paths generated during a plurality of substantially 360° scans by the source-detector assemblies 24, 26 as plotted in the $(\phi, \gamma)$ plane. FIG. 9c represents a flow diagram illustrating a complete operating sequence for collecting data at the measurement points required for exact reconstruction.

The source 24 provides a fan-shaped beam spanning a twenty-degree angle. In FIG. 9a the beams b1, b2 represent the field center line of the radiation field produced by the plurality of beams. The X-ray tube 100 is oriented to provide the 20° beam through the cross-section of the specimen and a plurality of source collimators divides the fan-shaped beam into 20 collimated beams. Each beam is collimated to a width of approximately 1/6°. An aligned twenty detector array is characterized by the separation angle $\alpha$ between adjacent detectors of one degree. This combination allows measurements of the angle $\phi$ in a 20° arc every one degree without actual rotation of the pair 24, 26.

For increased resolution, the pair 24, 26 is rotated by increments, one increment per orbit until one beam has incrementally swept through an angle $\phi$ of one degree. In the illustration shown in Table I measurements are taken at every angle $\gamma$ which is a multiple of 1° and at every angle $\phi$ which is a multiple of 0.167°. This results in a set of 120 linear data points at 180 different angles spanning the cross-section of the patient. Increasing the number of incremental rotations in the angle $\phi$ increases the number of data points and thus provides increased resolution. Measurements may also be made at $\gamma$ increments less than 1° to increase the number of angular views thus providing increased resolution. The preferred embodiment provides 180 views, using an approximate 359° orbital rotation.

For this mode of operation, the patient under study is positioned on the stretcher 14 between the source-detector assemblies 24, 26. FIG. 9a shows a hypothetical cross-section of the patient substantially centered (about the shaft 48) to provide an effective system axis passing through the patient about which the source-detector assemblies 24, 26 orbit. Table I sets out the angle $\phi$, $\gamma$ at which measurements are desired for an array of 20 detectors, and an angle $\alpha$ of 1° between adjacent detectors, with the distance $d$ between the origin and the source axis equal to 70 cm. The increment in the rotation angle $\phi$ is a submultiple of the angle $\alpha$; for example ($\alpha/6 = .167°$. This schedule provides 200 × 180 data point matrix corresponding to $\Delta\theta$ equal to 1° and $\Delta t$ equal to .203 cm.

TABLE I

| $\phi$ | measure at $\gamma =$ |
|---|---|
| 0 | 0°, 1°, 2°, 3°, ... 179° |
| .167 | −179.833°, −178.833°, ... −.833° or 179.167°, 178.167°, ... 0.167° |
| .333 | 0.333°, 1.333°, ... 179.333° |
| .5 | −179.5°, −178.5°, ... −.5° or 179.5°, 178.5°, ... .5° |
| .667 | 0.667°, 1.667°, ... 179.667° |
| .833 | −179.167°, −178.167°, ... −.167° or 179.833°, 178.833°, ... .833° |

For $\alpha = 1°$, $\frac{\alpha}{n} = .167°$, $d = 70$ cm.

Referring to the operating sequence depicted in FIG. 9c, the source detector pair 24, 26 is initially adjusted so that the angles $\gamma, \phi$ equal 0. With the angle $\phi$ equal to 0, the source detector pair is rotated through an arc of 180° in the $\gamma$ direction.

During the first scan measurements are taken at angles N$\alpha$, where N = 0, 1, ..., 179. Therefore, during the first scan measurements are taken every integer number of degrees between 0° and 179°. When the angle $\gamma$ reaches 180° the angle of rotation $\phi$ is incremented by an angle $\Delta\Phi = \alpha/n$, where $n$ is any integer; choosing $n = 6$ as shown provides $\Delta\Phi = .167°$.

The source detector pair 24, 26 has rotated until the angle $\gamma = 180°$, it continues orbiting from −180° to 0° about the specimen, or it reverses direction and orbits from 180° to 0°. Measurements are taken at the angles $\gamma = -179.833°, -178.833°, ... .833°$, or at 179.167°, 178.167° ... .167° respectively. The angle of rotation $\phi$ is then incremented by another .167, and the process continues until the angle of rotation $\phi$ equals $\alpha$ or 1°. The scanning path in FIG. 9b is that of continuous rotation without direction reversal. This is the preferred scanning motion, as direction reversals are entirely eliminated. If the system 10 is operated to reverse motion in the $\gamma$ direction after every 180° scan, only five reversals are required for $n = 6$.

The scanning paths which are depicted in FIG. 9b and which are produced by the nonconcurrent scanning motions are duplicated by the system 10 in FIG. 1 when the source, detector translating motors 68, 70 are utilized instead of the detector assembly and pivot bracket rotating motors 62, 64. The set of X-ray beams is sequentially rotated about the origin 160 through a predetermined arc for each of a plurality of radial translations from the origin. Choosing $d = 70$ cm., an increment in the angle $\phi$ equal to .167° corresponds to a radial translation R equal to 70 sin .167 degrees or approximately 2.03mm with a 0.167° offset in the angle $\theta$.

More specifically, after a linear translation of the assemblies 24, 26, they are orbited by the support apparatus 28 through an arc of 180°. Referring to the scan sequence of FIGS. 9a–9c, the first scan, as described for the angle of rotation $\phi = 0$, is duplicated with a zero millimeter translation and orbit of the assemblies 24, 26. Measurements are taken at the angles $\gamma$ equal to 0, 1, 2, . . . 179°. The next scan, corresponding to the angle $\phi$ equal to 0.167° with measurements taken at 0.167°, 1.167° and, so forth, is duplicated with an approximate 2.03 millimeter linear translation of and orbit of the assemblies 24, 26. The next scan corresponding of 4.06 millimeters and so forth. The goal of minimizing accelerations and decelerations, and direction changes of the source, detector assemblies 24, 26 is again accomplished. Very little time is required to index the assemblies 24, 26 the approximate 2.03 millimeter increment between 180° arcs, and once the overall linear translation in one direction achieved, the study is finished.

359° Collection of Nonredundant Data (Backside Scanning)

The described theory of operation of the scanning apparatus 10 using nonconcurrent axial scanning provides nonredundant data through successive 179° orbits of the assemblies 24, 26 only if the assemblies 24, 26 are indexed in the $\phi$ direction after every 179° scan. This is because the tissues of the human body bidirectionally pass an X-ray beam substantially to the same extent. Accordingly, a beam passing through a particular point in the body at an initial angle $\theta$ equal to the zero degrees produces the same transmission or absorption coefficient as a beam passing through the same point produced at an angle $\theta$ equals 180°.

The previously described nonconcurrent scanning motions which orbit the assemblies 24, 26 through a complete orbit of 360°, however, are advantageous in that the "back" 180° may be used to increment the assemblies 24, 26 in the $\phi$ direction in preparation for the next scan.

Figure 10A:
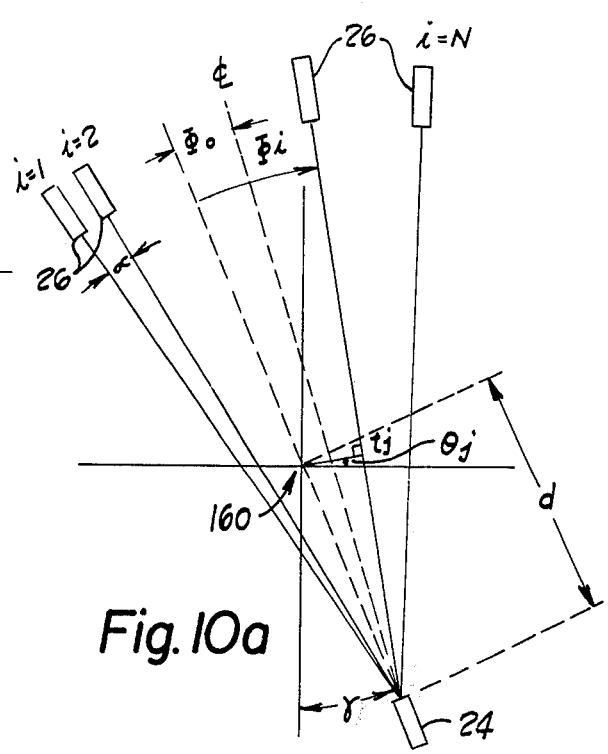
FIG. 10a is a diagram showing a multibeam source assembly having its field center offset by an offset angle $\Phi_o$ from the center of orbit for minimizing accelerations, decelerations, and direction reversals of the source assembly.
Figure 10B:
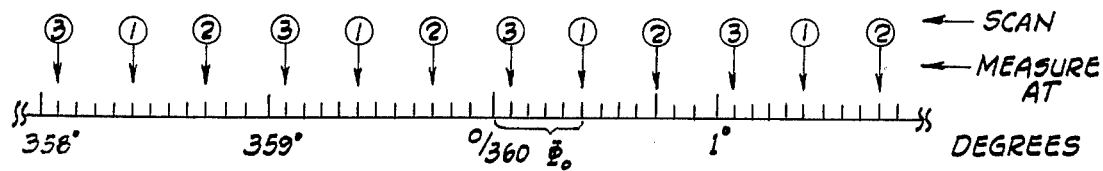
FIG. 10b is a bar chart of an exemplary scan showing the values of the orbit at which measurements are taken.

FIG. 10a depicts the N fan-shaped set of beams generated by the source assembly 24 having a rotational offset so that none of the individual beams pass through the origin 160. The detectors 26 are labeled $i = 1 \ldots N$ corresponding to the beams $i = 1 \ldots N$. Adjacent beams are separated by the separation angle $\alpha$ so that the radiation field spans $(N-1/2)\alpha°$ on each side of a field center $\mathcal{L}$. The source assembly 24 is positioned a distance $d$ from the origin 160 (the center of rotation).

Assuming that the beams are initially positioned with the field center $\mathcal{L}$ passing through the origin 160, the assemblies 24, 26 are rotated through an offset angle $\Phi_o$ about the source axis to effect an offset distance D between the origin 160 and the field center $\mathcal{L}$. By the proper selection of the offset distance D, orbiting of the assemblies 24, 26 will allow the detection of nonduplicated data through a complete orbit of approximately 359° without an acceleration or deceleration of the assemblies 24, 26 at $\gamma = 180°$. As the assemblies 24, 26 are rotated through the substantially 359 degrees orbit, the offset distance D (or the offset angle $\Phi_o$) is maintained. Because passage of the X-ray beam through the human body is substantially bidirectional, the orbiting with the offset provides a second complete set of nonduplicated data through the back 179°.

To produce reconstructed images of increased resolution, several 359° orbits may be performed. The offset distance D required to allow collection of nonduplicate data through the back 179° is given in Equation 8.

$$D = d \sin\left(\frac{b\alpha}{2} - \frac{\alpha}{4R}\right) \tag{8}$$

wherein R is the total number of orbits selected to constitute a complete study, and b is a number whose value is either a zero or a one depending respectively on whether the number N of detectors is odd or even.

As measured from an initial position of the assemblies with the field center coincident with the origin 160, the offset angle $\Phi_o$ is characterized by Equation 9.

$$\Phi_o = b\,\alpha/2 - \alpha/4R \qquad \text{EQN (9)}$$

After completion of each orbit the source and detector assemblies are rotated about the source axis by an incremental angle $\Delta\Phi$ as characterized substantially by Equation 10 or Equation 11.

$$\Delta\Phi = -\frac{\alpha}{R} \tag{10}$$

$$\Delta\Phi = -\frac{\alpha}{2R} \tag{11}$$

In Equation 10 the total number of orbits R is defined to mean the total number of substantially 359° orbital scans. Using the value of $\Delta\Phi = -\alpha/R$ provides an optimum data mix as a given detector in the detector assembly 26 measure alternate data points used in reconstructing the set of reconstruction points $m(t_k, \theta_n)$. This selection of the incremental angle $\Delta\Phi$ produces an interlacing of data points among the detectors.

For the embodiment wherein the incremental angle $\Delta\Phi$ equals $-\alpha/2R$, R may be either integer or half values of the number of 359° scans chosen to constitute the study. This choice of $\Delta\Phi$ results in a given detector measuring successive measurement points $m(t_k, \theta_n)$ used in the reconstruction.

During each orbit of the source and detector assemblies 24, 26, intensity measurements are taken at points in the orbit when the assemblies define the angle of rotation $\phi_j$ and the angle of orbit $\gamma_j$ substantially as characterized in Equations 12 and 13.

$$\phi_j = \sin^{-1}\left(\frac{k\Delta t}{d}\right) + \Phi_R \tag{12}$$

$$\gamma_j = \phi_j + n\Delta\theta \tag{13}$$

where $\Phi_R$ is characterized by Equation 14.

$$\Phi_R = \Phi_o + (r-1)\Delta\Phi \qquad \text{EQN (14)}$$

substantially a one revolution orbital path about the system axis during the study, and for maintaining the distance D substantially constant during an orbit of the source means and the detector means; and, e. data collection means, including said radiation detector means, for collecting values of intensities of said beams at predetermined orbital positions of said radiation source means and radiation detector means as about said orbital center, wherein said displacing said field line center by said predetermined distance D allows the collection of nonduplicate data throughout the substantial orbit of one revolution.

2. The scanning apparatus according to claim 1 wherein:
   a. said orbiting means comprises means for continuously rotating the radiation source means and the radiation detector means through an orbit of substantially 359°; and
   b. the data collection means comprises means for collecting the intensity of values at equal predetermined orbital positions.

3. The scanning apparatus according to claim 2 wherein said predetermined distance D is less than the value $d \sin \alpha/2$.

4. The scanning apparatus according to claim 3 wherein said predetermined distance D is described substantially according to the formula $$D = d \sin \left( b \frac{\alpha}{2} - \frac{\alpha}{4R} \right)$$

where R is the total number of orbits chosen to constitute a complete study and $b$ has a value equal to zero or one, respectively, depending on whether the number N of beams is an odd or even integer.

5. The scanning apparatus according to claim 4 wherein said radiation detector means includes a plurality of radiation detector assemblies respectively aligned with the beams of radiation, and said offsetting means includes rotation means for relatively rotating the source means and the detector means about the source axis, said rotation means being conditioned to rotate the source means and the detector means through an angle Φ characterized substantially as $$\Phi_o = \left( b \frac{\alpha}{2} - \frac{\alpha}{4R} \right).$$

6. The scanning apparatus according to claim 5 wherein said rotation means comprises means for relatively rotating the source means and the detector means through an angle ΔΦ in the plane at the end of each orbit and prior to a succeeding orbit, where ΔΦ is described substantially according to the formula $\Delta\Phi = -\alpha/R$.

7. The scanning apparatus according to claim 5 wherein said rotation means comprises means for relatively rotating the source means and the detector means through an angle ΔΦ at the end of each orbit and prior to a succeeding orbit, where ΔΦ is described substantially according to the formula $\Delta\Phi = -\alpha/2 R$.

8. The scanning apparatus according to claim 3 wherein the predetermined orbital positions are spaced approximately 1° or less from one another.

9. The scanning apparatus according to claim 5 wherein said data collection means comprises means for collecting data at values of angles of rotation $\phi_j$ about the source axis and of angles of orbit $\gamma_j$ about the system axis so that measurements are taken as a beam of radiation passes through points $(t_k, \theta_n)$ spaced about the system axis, the angles $\phi_j$, $\gamma_j$, characterized substantially as $$\phi_j = \sin^{-1}\left(\frac{k\Delta t}{d}\right) + \Phi_R \quad \text{and} \quad \gamma_j = \phi_j + n\Delta\theta$$

where $k$ and $n$ are integers including zero, $d$ is the separation between the system axis and the source axis, and $\Phi_R$ is characterized substantially by the equation $\Phi_R = \Phi_o + (i-1)\Delta\Phi$ where $i$ is a positive integer defining the number of the orbit in the set of R total orbits.

10. The scanning apparatus according to claim 2 wherein the predetermined distance D is described substantially by the equation $$D = d \sin \left( \left[\frac{N-1}{2}\right]\alpha + \frac{\alpha}{2R} \right),$$

where R is the total number of orbits chosen to constitute a complete study.

11. The scanning apparatus according to claim 10 wherein said radiation detector means includes a plurality of radiation detector assemblies respectively aligned with the beams of radiation, and said offsetting means includes rotating means for relatively rotating said source and detector means about the source axis.

12. The scanning apparatus according to claim 11 wherein said rotating means comprises means for relatively rotating the source and the detector means through an angle $\Phi_o$ about the source axis and described substantially according to the formula $$\Phi_o = \left[ \left(\frac{N-1}{2}\right)\alpha + \frac{\alpha}{2R} \right].$$

13. The scanning apparatus according to claim 12 wherein said means for rotating comprises means for relatively rotating the source and detector means through an angle ΔΦ about the source axis at the end of each orbit and prior to a succeeding orbit, the angle ΔΦ being described substantially according to the formula $\Delta\Phi = \alpha/R$.

14. The scanning apparatus according to claim 13 wherein the predetermined orbital positions are spaced approximately 1° or less from one another.

15. The scanning apparatus according to claim 11 wherein the data collection means comprises means for collecting data at values of angles of rotation $\phi_j$ about the source axis and at angles of orbit $\gamma_j$ about the system axis so that measurements are taken as a beam of radiation passes through points $(t(k), \theta(n))$ spaced about the system axis, the angles $\phi_j$, $\gamma_j$ characterized substantially as $$\phi_j = \sin^{-1}\left(\frac{k\Delta t}{d}\right) + \Phi_R \quad \text{and} \quad \gamma_j = \phi_j + n\Delta\theta$$

where $k$ and $n$ are integers, and $\Phi_R$ is determined according to the formula $\Phi_R = \Phi_o + (-1)\Delta\Phi$, where $i$ is a positive integer and is characterized by the number of the orbit in the sequence of R orbits performed during a study.

16. Apparatus for scanning an interior section of a body with a beam of X-radiation which passes through coplanar points $(t_k, \theta_n)$ in a plane containing such body section, wherein $k$, $n$ are integers including zero, comprising:
  a. radiation source and detector means including:
    i. a radiation source for providing a plurality of N radially directed beams of radiation, the outermost beams subtending a radiation field of $$\frac{N-1}{2}\alpha$$

on either side of a radiation field center line, where $\alpha$ is the angular separation between axes of the adjacent beams, and,
    ii. a plurality of radiation detectors in alignment with respective beams of radiation for measuring the respective intensity values of said beams;
  b. support structure for maintaining said radiation source and detector means in spaced alignment about a system axis as a study is conducted, said support structure including:
    i. rotating means for rotating said radiation source and detector means relatively about a source axis substantially passing through the radiation source, and for rotating the radiation source and detector means about the source axis until said field center line is offset from the system axis by an initial offset angle $\Phi_o$ wherein the angle $\Phi_o$ is characterized substantially by the formula $$\Phi_o = \frac{b\alpha}{2} - \frac{\alpha}{4R}$$

where R is the total number of orbits of the radiation source and detector means and $b$ has a value equal to zero of one, respectively, depending on whether the number N of beams is an odd or even integer, and,
    ii. orbiting means for orbiting the radiation source and detector means about the system axis through at least one substantially 359° orbital path during the study and for maintaining the value of the offset angle $\Phi_o$ during the orbiting; and,
  c. data collection means, including said radiation detectors, for measuring values of intensities of said beams at predetermined orbital positions of said radiation source and detector means, wherein said offset angle $\Phi_o$ all beams from the system axis and avoids the duplication of data throughout the entire substantially 359° orbit.

17. The scanning apparatus according to claim 16 wherein the source and detector means are orbited through a sequence of orbits and the rotating means comprises means for rotating the source and detector means about the source axis through an angle $\Delta\Phi$ after completion of each orbit and prior to the next in sequence orbit, the angle $\Delta\Phi$ characterized substantially by the equation $\Delta\Phi = -\alpha/R$

18. The scanning apparatus according to claim 16 wherein the source and detector means are rotated through a sequence of orbits and the rotating means comprises means for rotating the source and detector means about the source axis through an angle $\Delta\Phi$ after completion of each orbit and prior to the next in sequence orbit, the angle $\Delta\Phi$ characterized substantially by the equation $\Delta\Phi = -\alpha/2R$

19. The scanning apparatus according to claim 18 wherein said data collection means comprises for collecting data at values of angles of rotation $\phi_j$ about the source axis and of angles of orbit $\gamma_j$ about the system axis characterized substantially as $$\phi_j = \sin^{-1}\left(\frac{k\Delta t}{d} + \Phi_R\right) \quad \text{and} \quad \gamma_j = \phi_j + n\Delta\theta,$$

where $\Phi_R$ is characterized substantially by the equation $\Phi_R = \Phi_o + (i-1)\Delta\Phi$ where $i$ is a positive integer defining the number of the orbit in the set of R total orbits.

20. Apparatus for scanning an interior section of a body with a beam of X-radiation which passes through copolanar points $(t_k, \theta_n)$ in a plane containing such body section, wherein $k$, $n$ are integers including zero, comprising:
  a. radiation source and detector means including:
    i. a radiation source for providing a plurality of N radially directed beams of radiation, the outermost beams subtending a radiation field of $(N-1/2)\ \alpha°$ on either side of a radiation field center line, where $\alpha$ is the angular separation between axes of adjacent beams, and
    ii. a plurality of radiation detectors in alignment with respective beams of radiation for measuring the respective intensity values of said beams;
  b. support structure for maintaining said radiation source and detector means in spaced alignment about a system axis as a study is conducted, said support structure including:
    i. rotating means for rotating said radiation source and detector means relatively about a source axis substantially passing through the radiation source, and for rotating the radiation source and detector means about the source axis until said field center line is offset from the system axis by an initial offset angle $\Phi_o$ wherein the angle $\Phi_o$ is characterized substantially by the formula $\Phi_o = (N-1/2)\ \alpha + \alpha/2\ R$ wherein R is the total number of orbits of the radiation source and detector means, and
    ii. orbiting means for orbiting the radiation source and detector means about the system axis through at least one substantially 359° orbital path during the study and for maintaining the value of the offset angle $\Phi_o$ during the orbiting; and,
  c. data collection means, including said radiation detectors, for measuring values of intensities of said beams at predetermined orbital positions of said radiation source and detector means in said orbital path, wherein said offset angle $\Phi_o$ offsets all substantially a one revolution orbital path about the system axis during the study, and for maintaining the distance D substantially constant during an orbit of the source means and the detector means; and,
e. data collection means, including said radiation detector means, for collecting values of intensities of said beams at predetermined orbital positions of said radiation source means and radiation detector means as about said orbital center, wherein said displacing said field line center by said predetermined distance D allows the collection of nonduplicate data throughout the substantial orbit of one revolution.

2. The scanning apparatus according to claim 1 wherein:
   a. said orbiting means comprises means for continuously rotating the radiation source means and the radiation detector means through an orbit of substantially 359°; and
   b. the data collection means comprises means for collecting the intensity of values at equal predetermined orbital positions.

3. The scanning apparatus according to claim 2 wherein said predetermined distance D is less than the value $d \sin \alpha/2$.

4. The scanning apparatus according to claim 3 wherein said predetermined distance D is described substantially according to the formula $$D = d \sin \left( b \frac{\alpha}{2} - \frac{\alpha}{4R} \right)$$

where R is the total number of orbits chosen to constitute a complete study and $b$ has a value equal to zero or one, respectively, depending on whether the number N of beams is an odd or even integer.

5. The scanning apparatus according to claim 4 wherein said radiation detector means includes a plurality of radiation detector assemblies respectively aligned with the beams of radiation, and said offsetting means includes rotation means for relatively rotating the source means and the detector means about the source axis, said rotation means being conditioned to rotate the source means and the detector means through an angle $\Phi$ characterized substantially as $$\Phi_o = \left( b \frac{\alpha}{2} - \frac{\alpha}{4R} \right).$$

6. The scanning apparatus according to claim 5 wherein said rotation means comprises means for relatively rotating the source means and the detector means through an angle $\Delta\Phi$ in the plane at the end of each orbit and prior to a succeeding orbit, where $\Delta\Phi$ is described substantially according to the formula $\Delta\Phi = -\alpha/R$.

7. The scanning apparatus according to claim 5 wherein said rotation means comprises means for relatively rotating the source means and the detector means through an angle $\Delta\Phi$ at the end of each orbit and prior to a succeeding orbit, where $\Delta\Phi$ is described substantially according to the formula $\Delta\Phi = -\alpha/2R$.

8. The scanning apparatus according to claim 3 wherein the predetermined orbital positions are spaced approximately 1° or less from one another.

9. The scanning apparatus according to claim 5 wherein said data collection means comprises means for collecting data at values of angles of rotation $\phi_j$ about the source axis and of angles of orbit $\gamma_j$ about the system axis so that measurements are taken as a beam of radiation passes through points $(t_k, \theta_n)$ spaced about the system axis, the angles $\phi_j, \gamma_j$, characterized substantially as $$\phi_j = \sin^{-1}\left(\frac{k\Delta t}{d}\right) + \Phi_R \quad \text{and} \quad \gamma_j = \phi_j + n\Delta\theta$$

where $k$ and $n$ are integers including zero, $d$ is the separation between the system axis and the source axis, and $\Phi_R$ is characterized substantially by the equation $\Phi_R = \Phi_o + (i-1)\Delta\Phi$ where $i$ is a positive integer defining the number of the orbit in the set of R total orbits.

10. The scanning apparatus according to claim 2 wherein the predetermined distance D is described substantially by the equation $$D = d \sin \left( \left[ \frac{N-1}{2} \right] \alpha + \frac{\alpha}{2R} \right),$$

where R is the total number of orbits chosen to constitute a complete study.

11. The scanning apparatus according to claim 10 wherein said radiation detector means includes a plurality of radiation detector assemblies respectively aligned with the beams of radiation, and said offsetting means includes rotating means for relatively rotating said source and detector means about the source axis.

12. The scanning apparatus according to claim 11 wherein said rotating means comprises means for relatively rotating the source and the detector means through an angle $\Phi_o$ about the source axis and described substantially according to the formula $$\Phi_o = \left[ \left(\frac{N-1}{2}\right)\alpha + \frac{\alpha}{2R} \right].$$

13. The scanning apparatus according to claim 12 wherein said means for rotating comprises means for relatively rotating the source and detector means through an angle $\Delta\Phi$ about the source axis at the end of each orbit and prior to a succeeding orbit, the angle $\Delta\Phi$ being described substantially according to the formula $\Delta\Phi = \alpha/R$.

14. The scanning apparatus according to claim 13 wherein the predetermined orbital positions are spaced approximately 1° or less from one another.

15. The scanning apparatus according to claim 11 wherein the data collection means comprises means for collecting data at values of angles of rotation $\phi_j$ about the source axis and at angles of orbit $\gamma_j$ about the system axis so that measurements are taken as a beam of radiation passes through points $(t(k), \theta(n))$ spaced about the system axis, the angles $\phi_j, \gamma_j$ characterized substantially as $$\phi_j = \sin^{-1}\left(\frac{k\Delta t}{d}\right) + \Phi_R \quad \text{and} \quad \gamma_j = \phi_j + n\Delta\theta$$

where $k$ and $n$ are integers, and $\Phi_R$ is determined according to the formula $\Phi_R = \Phi_o + (-1)\Delta\Phi$, where $i$ is a positive integer and is characterized by the number of the orbit in the sequence of R orbits performed during a study.

16. Apparatus for scanning an interior section of a body with a beam of X-radiation which passes through coplanar points $(t_k, \theta_n)$ in a plane containing such body section, wherein $k$, $n$ are integers including zero, comprising:
   a. radiation source and detector means including:
      i. a radiation source for providing a plurality of N radially directed beams of radiation, the outermost beams subtending a radiation field of $$\frac{N-1}{2}\alpha$$

on either side of a radiation field center line, where $\alpha$ is the angular separation between axes of the adjacent beams, and,
      ii. a plurality of radiation detectors in alignment with respective beams of radiation for measuring the respective intensity values of said beams;
   b. support structure for maintaining said radiation source and detector means in spaced alignment about a system axis as a study is conducted, said support structure including:
      i. rotating means for rotating said radiation source and detector means relatively about a source axis substantially passing through the radiation source, and for rotating the radiation source and detector means about the source axis until said field center line is offset from the system axis by an initial offset angle $\Phi_o$ wherein the angle $\Phi_o$ is characterized substantially by the formula $$\Phi_o = \frac{b\alpha}{2} - \frac{\alpha}{4R}$$

where R is the total number of orbits of the radiation source and detector means and $b$ has a value equal to zero of one, respectively, depending on whether the number N of beams is an odd or even integer, and,
      ii. orbiting means for orbiting the radiation source and detector means about the system axis through at least one substantially 359° orbital path during the study and for maintaining the value of the offset angle $\Phi_o$ during the orbiting; and,
   c. data collection means, including said radiation detectors, for measuring values of intensities of said beams at predetermined orbital positions of said radiation source and detector means, wherein said offset angle $\Phi_o$ all beams from the system axis and avoids the duplication of data throughout the entire substantially 359° orbit.

17. The scanning apparatus according to claim 16 wherein the source and detector means are orbited through a sequence of orbits and the rotating means comprises means for rotating the source and detector means about the source axis through an angle $\Delta\Phi$ after completion of each orbit and prior to the next in sequence orbit, the angle $\Delta\Phi$ characterized substantially by the equation $\Delta\Phi = -\alpha/R$ 18. The scanning apparatus according to claim 16 wherein the source and detector means are rotated through a sequence of orbits and the rotating means comprises means for rotating the source and detector means about the source axis through an angle $\Delta\Phi$ after completion of each orbit and prior to the next in sequence orbit, the angle $\Delta\Phi$ characterized substantially by the equation $\Delta\Phi = -\alpha/2R$ 19. The scanning apparatus according to claim 18 wherein said data collection means comprises for collecting data at values of angles of rotation $\phi_j$ about the source axis and of angles of orbit $\gamma_j$ about the system axis characterized substantially as $$\phi_j = \sin^{-1}\left(\frac{k\Delta t}{d} + \Phi_R\right) \quad \text{and} \quad \gamma_j = \phi_j + n\Delta\theta,$$

where $\Phi_R$ is characterized substantially by the equation $\Phi_R = \Phi_o + (i-1)\Delta\Phi$ where $i$ is a positive integer defining the number of the orbit in the set of R total orbits.

20. Apparatus for scanning an interior section of a body with a beam of X-radiation which passes through copolanar points $(t_k, \theta_n)$ in a plane containing such body section, wherein $k$, $n$ are integers including zero, comprising:
   a. radiation source and detector means including:
      i. a radiation source for providing a plurality of N radially directed beams of radiation, the outermost beams subtending a radiation field of $(N-1/2)\ \alpha°$ on either side of a radiation field center line, where $\alpha$ is the angular separation between axes of adjacent beams, and
      ii. a plurality of radiation detectors in alignment with respective beams of radiation for measuring the respective intensity values of said beams;
   b. support structure for maintaining said radiation source and detector means in spaced alignment about a system axis as a study is conducted, said support structure including:
      i. rotating means for rotating said radiation source and detector means relatively about a source axis substantially passing through the radiation source, and for rotating the radiation source and detector means about the source axis until said field center line is offset from the system axis by an initial offset angle $\Phi_o$ wherein the angle $\Phi_o$ is characterized substantially by the formula $\Phi_o = (N-1/2)\ \alpha + \alpha/2\ R$ wherein R is the total number of orbits of the radiation source and detector means, and
      ii. orbiting means for orbiting the radiation source and detector means about the system axis through at least one substantially 359° orbital path during the study and for maintaining the value of the offset angle $\Phi_o$ during the orbiting; and,
   c. data collection means, including said radiation detectors, for measuring values of intensities of said beams at predetermined orbital positions of said radiation source and detector means in said orbital path, wherein said offset angle $\Phi_o$ offsets all the beams from the system axis and avoids duplication of data throughout the entire 359° orbit.

21. The scanning apparatus according to Claim 20 wherein the source and detector means are orbited through a sequence of orbits and the rotating means comprises means for rotating the source and detector means about the source axis through an angle $\Delta \Phi$ after completion of each orbit and prior to the next in sequence orbit, the angle $\Delta \Phi$ characterized substantially by the equation $\Delta \Phi = \alpha/R$.

22. The scanning apparatus according to Claim 21 wherein said data collection means comprises means for collecting data at values of angles of rotation $\phi_j$ about the source axis and of angles of orbit $\gamma_j$ about the system axis characterized substantially as $\phi_j = \sin^{-1}(k\Delta t/d + \Phi_R)$ and $\gamma_j = \phi_j + n \Delta \theta$, where $\Phi_R$ is characterized substantially by the equation $\Phi_R = \Phi_o + (i-1) \Delta \Phi$ where $i$ is a positive integer defining the number of the orbit in the set of R total orbits.

23. A method of scanning planar points $(t_k, \theta n)$ of an interior section of a body with a set of coplaner beams directed substantially radially of a radiation source in the plane of said points to an array of N aligned radiation detectors wherein the radiation source means is orbital about a system axis and in said plane, adjacent detectors in said array are separated by an angle $\alpha$, the set of beams providing a radiation field of scan of $(N-1) \alpha/2$ degrees on each side of a radiation field center line, the beams thereby spanning $(N-1) \times \alpha$ degrees in the plane where N is an integer and the radiation source means is a distance d from the system axis, comprising the steps of:
  a. relatively displacing the radiation source and said system axis to offset the field center line a predetermined mined transverse distance D from the system axis thereby causing all beams of radiation to be offset from the system axis;
  b. orbiting said source means through at least one arc of substantially one complete revolution about the system axis while maintaining the displacement of said distance D; and,
  c. measuring the intensity of each beam after it passes through the body at predetermined orbital positions throughout the one complete revolution about the system axis, said transverse distance D allowing the collection of nonduplicate data throughout the entire orbit.

24. The method according to claim 23 wherein said step of orbiting comprises the step of orbiting said source continuously through at least 359°.

25. The method of scanning according to claim 24 wherein said step of relatively displacing the radiation source means comprises the step of relatively displacing the field center line by a distance substantially characterized by the equation $D = d \sin(b\alpha/2 - \alpha/4R)$ where R is the total number of orbits chosen to constitute a complete study and $b$ has a value equal to zero or one, respectively, depending on whether the number N of detectors is an odd or even integer.

26. The method of scanning according to claim 24 wherein said step of relatively displacing the radiation source means comprises the step of relatively displacing the field center line by a distance substantially characterized by the equation $$D = d \sin(((N-1) \alpha/2) + (\alpha/2R)),$$

where R is the total number of orbits chosen to constitute a study.

27. The method of scanning according to claim 25 wherein the step of measuring comprises the step of measuring at incremental angles of $\gamma$ substantially equal to one degree or less about the system axis.

28. The method of scanning according to claim 26 wherein said step of measuring comprises the step of measuring at incremental angles of $\gamma$ substantially equal to one degree or less about the system axis.

29. The method of scanning according to claim 25 wherein said step of relatively displacing comprises the step of rotating said radiation source means through an angle $\Phi_o$ about a source axis effectively passing through the source means, the angle $\Phi_o$ being substantially characterized by the equation $\Phi_o = b \alpha/2 - \alpha/4R$.

30. The method of scanning according to claim 25 wherein said step of relatively displacing comprises the step of rotating said radiation source means through an angle $\Phi_o$ about a source axis effectively passing through the source means, the angle $\Phi_o$ being substantially characterized by the equation $\Phi_o = (N-1/2) \alpha + \alpha/2R$.

31. The method of scanning according to claim 29 wherein said step of orbiting includes orbiting through a sequence of substantially 359 degree arcs and further including the step of incrementally rotating the radiation source means through an angle $\Delta\Phi$ about the source axis after every orbit and prior to a next in sequence orbit.

32. The method of scanning according to claim 30 wherein said step of orbiting includes orbiting through a sequence of substantially 359° arcs and further including the step of incrementally rotating the radiation source means through an angle $\Delta\Phi$ about the source axis after every orbit and prior to a next in sequence orbit.

33. The method of scanning according to claim 31 wherein $\Delta\Phi$ is characterized substantially as $\Delta\Phi = -\alpha/2R$.

34. The method of scanning according to claim 31 wherein $\Delta\Phi$ is characterized substantially as $\Delta\Phi = -\alpha/R$.

35. The method of scanning according to Claim 32 wherein $\Delta\Phi$ is characterized substantially as $\Delta\Phi = \alpha/R$.

36. The method of scanning according to Claim 31 wherein said step of measuring comprises the step of measuring at values of angles $\phi_j$ of rotation and angles $\gamma_j$ of orbit characterized substantially by the equation $$\phi_j = \sin^{-1}\left(\frac{k\Delta t}{d} + \Phi_R\right) \text{ and } \gamma_j = \phi_j + n\Delta\theta,$$

wherein $\Phi_R$ is determined substantially according to the formula $\Phi_R = \Phi_o + (i-1) \Delta\Phi$ where $i$ is a positive integer and is characterized by the number of the orbit in the sequence of R orbits performed during the study.

37. The method of scanning according to Claim 32 wherein said step of measuring comprises the step of measuring at values of angles $\phi_j$ of rotation and angles $\gamma_j$ of orbit characterized substantially by the equation $$\phi_j = \sin^{-1}\left(\frac{k\Delta t}{d} + \Phi_R\right) \quad \gamma_j = \phi_j + n\Delta\theta;$$

wherein $\Phi_R$ is determined substantially according to the formula $\Phi_R = \Phi_o + (i-1) \Delta\Phi$ where $i$ is a positive integer and is characterized by the number of the orbit in the sequence of R orbits performed during the study.

38. A method of successively scanning the interior section of a body with a set of N coplanar beams of X-rays for determining the coefficient of absorption or transmission at points ($t_k$, $\theta_n$) spaced about a center of rotation lying in the plane of the X-rays, the set of beams emanating from a source and detected by an array of N detectors in a source-detector assembly which maintains each detector diametrically spaced about the center of rotation and in alignment with the source and which maintains each detector separated by $\alpha$ degrees from an adjacent detector, the N beams providing a radiation field of N−1/2 ° on each side of a radiation field center line, the assembly being rotatable to define angles $\gamma_j$ about the center of orbit for orbiting the source and the detection through a total of R orbits, and further being rotatable to define an angle $\phi_j$ about a source axis substantially passing through the source, the method comprising the steps of:
   a. incrementally rotating the source-detector assembly about the source axis in a first rotational direction until the field center line is displaced from the center of orbit by an offset angle $\Phi_o$ substantially equal to ½ (N−1) $\alpha$ + $\alpha$/2R;
   b. continuously rotating said assembly through an orbital angle $\gamma$ of at least 359 ° about the center of orbit; and,
   c. measuring the intensity of said beam at the angles $\phi_j$, $\gamma_j$ substantially characterized as $$\phi_j = \sin^{-1}\left(\frac{k\Delta t}{d}\right) + \Phi_o \text{ and } \gamma_j = \phi_j + n\Delta\theta,$$

wherein $k$ and $n$ are integers including zero, and said offset angle $\Phi_o$ allows the collection of nonduplicate data during the entire 359° orbit.

39. The method of scanning according to claim 38 wherein said steps of continuously rotating said assembly and measuring are repeating steps and further including after each step of measuring and prior to the next repeating step of rotating, the step of rotating said source-detector assembly through an angle $\Delta\Phi$ about the source axis and of value $\alpha$/R.

40. The method of scanning according to claim 39 wherein said repeating step of measuring comprises the step of measuring at the angles $\phi_j$, $\gamma_j$ characterized substantially as $$\phi_j = \sin^{-1}\left(\frac{k\Delta t}{d}\right) + \Phi_o + \Delta\Phi; \gamma_j = \phi_j + n\Delta\theta.$$

41. A method of successively scanning the interior section of a body with a set of N coplanar beams of X-rays for determining the coefficient of absorption or transmission at points ($t_k$, $\theta_n$) spaced about a center of rotation lying in the plane of the X-rays, the set of beams emanating from a source and detected by an array of N detectors in a sourcedetector assembly which maintains each detector diametrically spaced about the center of rotation and in alignment with the source and which maintains each detector separated by $\alpha°$ from an adjacent detector, the N beams providing a radiation field of N−1/2° on each side of a radiation field center, the assembly being rotatable to define angles $\gamma_j$ about the center of orbit for orbiting the source and the detection through a total of R orbits, and further being rotatable to define an angle $\phi_j$ about a source axis substantially passing through the source, the method comprising the steps of:
   a. incrementally rotating the source-detector assembly about the source axis in a first rotational direction until the field center is displaced from the center of orbit by an offset angle $\Phi_o$ substantially equal to $$\frac{b\alpha}{2} - \frac{\alpha}{4R}$$

where $b$ has a value of zero or one, respectively, depending on whether the number N of detectors is an odd or even integer;
   b. continuously rotating said assembly through an orbital angle $\gamma$ of at least 359° about the center of orbit; and,
   c. measuring the intensity of said beam at the angles $\phi_j$, $\gamma_j$ substantially characterized as $$\phi_j = \sin^{-1}\left(\frac{k\Delta t}{d}\right) + \Phi_o \text{ and } \gamma_j = \phi_j + n\Delta\theta,$$

wherein $k$ and $n$ are integers including zero, and said offset angle $\Phi_o$ allows the collection of nonduplicate data during the entire 359° orbit.

* * * * *

UNITED STATES PATENT OFFICE
CERTIFICATE OF CORRECTION

Patent No. 4,008,400          Dated February 15, 1977

Inventor(s) Carl J. Brunnett et al.

It is certified that error appears in the above-identified patent and that said Letters Patent are hereby corrected as shown below:

Col. 4, line 63, delete "d ees"
Col. 4, line 12, "amont" should be -- among --
Col. 4, line 63; Col. 23, line 56; Col. 32, line 36; "(N-1/2)$\alpha$°" should be -- $\frac{N-1}{2}\alpha°$ --
Col. 6, line 6, after "$D_1 =$" delete "d sin"
Col. 12, lines 47-48, delete "support arm 50. The guides 118 maintain the detector"
Col. 17, line 41, "pluraity" should be -- plurality --
Col. 19, line 36, "the" second occurrence, should be -- a --
Col. 22, line 16, after "example" delete -- ( --
Col. 24, line 23, after "center" insert -- $\ell$ --
Col. 26, line 48, after "to" delete "d"
Col. 26, line 64, "16" should be -- 160 --
Col. 26, line 68, after "of" delete "2 d tan"
Col. 28, line 50; "N-1/2$\alpha$°" should be -- $\frac{N-1}{2}\alpha°$ --
Col. 31, line 7 "$\Phi_o+(-1)$ should be -- $\Phi_o+(i-1)$ --
Col. 31, line 21, after "$\alpha$" insert -- ° --
Col. 31, line 50, after "zero", "of" should be -- or --
Col. 32, line 29, "copolanar" should be -- coplanar --
Col. 32, line 55; Col. 34, line 20, "(N-1/2)$\alpha$" should be -- $\left(\frac{N-1}{2}\right)\alpha$ --
Col. 33, line 1, delete "the" first occurrence

UNITED STATES PATENT OFFICE
CERTIFICATE OF CORRECTION

Patent No. 4,008,400  Dated February 15, 1977

Inventor(s) Carl J. Brunnett et al.

It is certified that error appears in the above-identified patent and that said Letters Patent are hereby corrected as shown below:

Col. 33, line 35, delete "mined" second occurrence
Col. 33, line 65 "D =d sin (((N-1)α/2)+(α/2R))" should be -- $D = d \sin\left(\frac{(N-1)\alpha}{2} + \frac{\alpha}{2R}\right)$ --
Col. 35, line 14; Col. 36, line 17, "N-1/2°" should be -- $\frac{N-1}{2}°$ --
Col. 36, line 12, "sourcedetector" should be -- source-detector --
Col. 32, line 14, after "comprises" insert -- means --

Signed and Sealed this

Thirteenth Day of September 1977

[SEAL]

Attest:

RUTH C. MASON
Attesting Officer

LUTRELLE F. PARKER
Acting Commissioner of Patents and Trademarks